United States Patent
Mazzone et al.

(10) Patent No.: US 11,466,270 B2
(45) Date of Patent: Oct. 11, 2022

(54) MEANS AND METHODS TO TREAT INFLAMMATORY DISEASES

(71) Applicants: VIB VZW, Ghent (BE); Katholieke Universiteit Leuven, K.U. Leuven R&D, Leuven (BE)

(72) Inventors: Massimiliano Mazzone, Ghent (BE); Anne-Theres Henze, Averbode (BE)

(73) Assignees: VIB VZW, Ghent (BE); KATHOLIEKE UNIVERSITEIT LEUVEN, K.U. LEUVEN R & D, Leuven (BE)

( * ) Notice: Subject to any disclaimer, the term of this patent is extended or adjusted under 35 U.S.C. 154(b) by 751 days.

(21) Appl. No.: 16/332,575

(22) PCT Filed: Oct. 3, 2017

(86) PCT No.: PCT/EP2017/075039
§ 371 (c)(1),
(2) Date: Mar. 12, 2019

(87) PCT Pub. No.: WO2018/065390
PCT Pub. Date: Apr. 12, 2018

(65) Prior Publication Data
US 2021/0087554 A1 Mar. 25, 2021

(30) Foreign Application Priority Data
Oct. 4, 2016 (EP) .................................... 16192213

(51) Int. Cl.
C12N 15/113 (2010.01)
A61P 31/00 (2006.01)
A61P 33/02 (2006.01)
C12Q 1/6876 (2018.01)

(52) U.S. Cl.
CPC ............ *C12N 15/113* (2013.01); *A61P 31/00* (2018.01); *A61P 33/02* (2018.01); *C12Q 1/6876* (2013.01); *C12N 2310/113* (2013.01); *C12Q 2600/136* (2013.01); *C12Q 2600/158* (2013.01)

(58) Field of Classification Search
None
See application file for complete search history.

(56) References Cited

U.S. PATENT DOCUMENTS

2016/0040161 A1* 2/2016 Packard .................... A61P 9/00
514/44 A
2017/0304368 A1* 10/2017 Marban ................ C12N 5/0657

FOREIGN PATENT DOCUMENTS

CN 105617398 A 6/2016
WO WO-2014036429 A1 * 3/2014 ........... C12N 15/113

OTHER PUBLICATIONS

Henze Mir-210 at the crossroad of M2 and M1 macrophage polarization: retrieved on line on Jan. 19, 2022 from https://researchportal.be/en/project/mir-210-crossroad-m2-and-m1-macrophage-polarization-relevance-sepsis-and-cancer, pp. 1-3 (Year: 2022).*
English machine translation of specification, CN 105617398, pp. 1-24 (Year: 2016).*
English machine translation of claims, CN 105617398, pp. 1-2 (Year: 2016).*
Barnett et al., "Anti-inflammatory effects of miR-21 in the macrophage response to peritonitis," Journal of Leukocyte Biology, vol. 99, pp. 361-371, Sep. 2015.
International Search Report issued in application No. PCT/EP2017/075039 dated Jan. 3, 2018.
Monteiro et al., "Mir-190b negatively contributes to the Trypanosoma cruzi-infected cell survival by repressing PTEN protein expression," Mem. Inst. Oswaldo Cruz, vol. 110, No. 8, pp. 996-1002, Dec. 2015.
Nielsen et al., "Circulating Levels of MicroRNA from Children with Newly Diagnosed Type I Diabetes and Healthy Controls: Evidence that miR-25 Associates to Residual Beta-Cell Function and Glycaemic Control during Disease Progression," Experimental Diabetes Research, vol. 2012, Article ID 896362, Jan. 2012.
Osipova et al., "Diabetes-Associated MicroRNAs in Pediatric Patients With Type I Diabetes Mellitus: A Cross-Sectional Cohort Study," J. Clinc. Endocrinol. Metab., vol. 99, No. 9, pp. E1661-E1665, Sep. 2014.
Qi et al., "microRNA-210 negatively regulates LPS-induced production of proinflammatory cytokines by targeting NF-kB1 in murine macrophages," FEBS Letters, vol. 586, No. 8, pp. 1201-1207, Mar. 2012.
Simo et al., "Micro RNA expression profiles in peripheral blood cells of rats that were experimentally infected with *Trypanosoma congolense* and different *Trypanosoma brucei* subspecies," Microbes and Infection, vol. 17, pp. 596-608, Mar. 2015.
Zhang et al., "MiR-210 inhibits NF-kB signaling pathway by targeting DR6 in osteoarthritis," Scientific Reports, vol. 5, No. 1, p. 12775, Aug. 2015.

* cited by examiner

*Primary Examiner* — Brian Whiteman
(74) *Attorney, Agent, or Firm* — Rouget F. Henschel; Potomac Law Group, PLLC

(57) ABSTRACT

The present application relates to the field of inflammatory diseases, particularly to inflammatory diseases characterized by an M1 macrophage response, even more particularly to sepsis and to *Trypanosoma* infection. The invention provides substances modulating miR210 expression and/or activity, in particular RNA molecules inhibiting miR210 expression and/or activity and medical uses of these miR210 inhibitors. Methods are disclosed to screen for medicaments for treating sepsis.

5 Claims, 11 Drawing Sheets

Specification includes a Sequence Listing.

MEANS AND METHODS TO TREAT INFLAMMATORY DISEASES

FIELD OF THE INVENTION

The present application relates to the field of inflammatory diseases, particularly to inflammatory diseases characterized by an M1 macrophage response, even more particularly to sepsis and to *Trypanosoma* infection. It is disclosed that loss of miR210 expression reduces the severity of symptoms associated with sepsis and *Trypanosoma brucei* infection. The invention provides substances modulating miR210 expression and/or activity, in particular RNA molecules inhibiting miR210 expression and/or activity and medical uses of these miR210 inhibitors. Methods are disclosed to screen for medicaments for treating sepsis.

BACKGROUND

Inflammation is a response of the innate immune system and is triggered by stimuli such as infections, tissue injury and tissue stress with malfunction. Controlled inflammation, for example protection against a microbial infection in the host, is beneficial as it is an adaptive response to restore homeostasis. An inflammatory response is characterized by local dilatation of the blood vessels to increase the blood supply and by an increase of the intracellular spaces to stimulate the movement of leukocytes, proteins, pro-inflammatory molecules and fluid into the damaged tissue. This results in symptoms such as heat, pain, redness and swelling. Once the initial cause of cell injury is removed the body's immune system returns to a steady-state situation.

In sepsis, the immune system goes into overdrive, and the chemicals it releases into the blood to combat the infection trigger widespread inflammation that can ravage the entire body (Recknagel et al. 2012, PLoS Med 9: e1001338). Sepsis is characterized by hyper (>38° C.) or hypothermia (<36° C.), tachycardia (>90 beats/minute), tachypnea (>20 breaths/minute or $P_aCO_2$<32 mmHg) and leukocytosis/leukopenia (white blood cell count >12000/mm$^3$ or <4000/mm$^3$) (Rittirsch et al. 2007, J Leukoc Biol 81:137-143). Sepsis is thus caused by an inappropriate immune response and when it goes along with an organ dysfunction and symptoms such as hypoxemia, oliguria, hypotension, metabolic acidosis and thrombocytopenia it is defined as severe sepsis. Severe sepsis is a global clinical problem and it is the most important cause of mortality and morbidity in surgical intensive care units. The high mortality rate of sepsis is due to the early failure of several organ systems. The most common abnormalities that are associated with early sepsis related death are downregulation of the neurological, coagulation and renal function (Russell et al. 2008, Crit Care Med 28:3405-3411). The most life-threatening complications of sepsis are septic shock (in case of hypotension) and the multiorgan dysfunction syndrome. The mortality rate for severe sepsis is between 25 and 30% and between 40 and 70% for patients who suffer from septic shock (Nyström 1998, J Anitmicrob Chemother Suppl A: 1-7; Bernard et al. 2001, N Eng J Med 344: 699-709; Annane et al. 2003, Am J Respir Crit Care Med 168: 165-172).

There are several models to study sepsis in animals. First of all, there are the ones that induce sepsis by injecting an exogenous toxin, like LPS (lipopolysaccharide). LPS originates from Gram-negative bacteria. In the outer membrane of the cell envelope these bacteria have an endotoxin of which the main biological active component is LPS (Rietschel et al. 1996, Curr Top Microbiol Immunol 216: 39-81). LPS can form a complex with the LPS binding protein and bind to the TLR4 and CD14 on the cell membrane of macrophages and some other cell types. This triggers an inflammatory response with upregulation of pro-inflammatory cytokines like TNFα and IL-1β (Ulevitch & Tobias 1999, Curr Opin Immunol 11: 19-22; Poltorak et al. 1998, Science 282: 2085-2088; Lu et al. 2008, Cytokine 42:145-151). When LPS is injected intravascularly or in the peritoneum of animals, it can mimic the initial clinical steps of sepsis in humans and increase the pro-inflammatory cytokine levels (Doi et al. 2009, J Clin Invest 2: 422-430; Wichterman et al. 1980, J Surg Res 29: 189-201; Michie et al. 1988, N Engl J Med 318: 1481-1486). The second group of sepsis models contains the cecal ligation and puncture (CLP) model. In this case surgery is performed to create animals that suffer from sepsis. The cecum of the animal is ligated just below the ileocecal valve and then two times punctured with a needle. The endogenous protective barrier of the animals is changed and the leakage of intestinal fluid causes sepsis in the animal (Hubbard et al. 2005, Shock 24 Suppl 1:52-57). The sepsis models where there is infusion of exogenous live bacteria are classified in a third group (Doi et al. 2009, J Clin Invest 2: 422-430; Buras et al. 2005, Nat rev Drug Discov 4: 854-865; Wichterman et al. 1980, J Surg Res 29: 189-201). The LPS-induced inflammation model and the CLP model are mostly used for studying sepsis (Rittirsch et al. 2007, J Leukoc Biol 81: 137-143; Doi et al. 2009, J Clin Invest 2: 422-430).

In the immune response (of which a failure causes sepsis), macrophages play an extremely important role. Macrophages are a type of white blood cell that engulfs and digests cellular debris, foreign substances, microbes, cancer cells, and anything else that does not have the types of proteins specific of healthy body cells on its surface, in a process called phagocytosis. Besides phagocytosis, they play a critical role in nonspecific defense (innate immunity) and also help initiate specific defense mechanisms (adaptive immunity) by recruiting other immune cells such as lymphocytes. For example, they are important as antigen presenters to T cells. Beyond increasing inflammation and stimulating the immune system, macrophages also play an important anti-inflammatory role and can decrease immune reactions through the release of cytokines. The process, which defines the functional state of macrophages and determines which functional program is expressed in response to specific micro-environmental signals is called macrophage polarization. In most of the studies, polarized macrophages are classified in two major classes: M1 (classically activated) and M2 (alternatively activated) macrophages. These two classes mirror the Th1/Th2 cells paradigm of T-cells (Sica & Mantovani 2012, J Clin Invest 122:787-795; Gordon & Martinez 2010, Immunity 32:593-604; Lawrence & Natoli 2011, Nat Rev Immunol 11:750-761). The M1/M2 paradigm is shifted to the M1 polarization state in response to bacterial infections. M1 macrophages usually protect the host against bacterial infections by responding to type I inflammatory cytokines such as IFN-γ and IL-12 or microbial products like LPS. Inflammation leads to upregulation of genes involved in M1 polarization of macrophages, which differentiates macrophages into an M1-like phenotype. This group of upregulated genes encodes for pro-inflammatory cytokines such as IL-1β and TNFα, cytokine-receptors like the interleukin 7 receptor (IL-7R), the chemokine (C-C) motif ligand (CCL2), the C-C chemokine receptor 7 (CCR7), IFN-γ, IL-12 and IL-23. Genes that encode the reactive nitrogen enzyme NO synthase 2 (NOS 2) and indoleamine-pyrrole 2,3 dioxygenase (IDO), which is a reactive oxygen enzyme, are also upregulated in M1 shifted macrophages. Macrophages with the M1 phenotype are additionally characterized by a promotion of the Th1 response and a strong tumoricidal activity (Lawrence & Natoli 2011, Nat Rev Immunol 11:750-761; Benoit et al. 2008, J Immunol 181: 3733-3739). M2 macrophages are in comparison to M1 macrophages activated by different stimuli (i.e. TGF-β, IL-4, IL-13, IL-10). There are differences in receptor, cytokine and chemokine expression as well as in their effector functions. Type 2 polarized macrophages are activated in response to alternatively activation markers and are important for e.g. IL-10, TGF-β.

Given the high medical need for a treatment for sepsis, it is advantageous to study molecular pathways that are involved in sepsis and to develop molecules that can be used for treating sepsis and related infections characterized by an M1 macrophage response. In order to develop new strategies to combat inflammation, we approached sepsis as a hypoxia associated condition. Earlier results of a microarray in breast (MCF7 and MDA-MB231) and colon (HT29 and HCT116) cancer cell lines revealed that the expression of a specific group of microRNAs (miRNAs or miR), called hypoxamiRs, is induced in hypoxic regions (Kulshreshtha et al 2007, Mol Cell Biol 27: 1859-1867). This group contains miR-23, miR-24, miR-26, miR-27, miR-103, miR-107, miR-181, miR-210 and miR-213, with miR-210 as the most prominent one. MicroRNAs are small noncoding RNAs that pair to sites in mRNAs to regulate gene expression in eukaryotes and play important roles in a variety of cellular functions as well as in several diseases. In current application it is disclosed that the expression level of miR-210 is highly induced upon treatment with M1 cytokines and downregulated upon M2 cytokine treatment. Moreover, reducing the expression level of miR-210 in a genetic and/or pharmaceutical way improved the survival rate of a sepsis mice model as well as that of mice that were infected with *Trypanosoma brucei*.

miR-210 is a widely studied molecule. Both upregulation of miR-210 expression and genetic deletions have been linked with several types of cancer (Chan & Loscalzo 2010, Cell Cycle 9:1072-1083; Ho et al. 2013, Translational Oncology 3:109-113). miR-210 has also been demonstrated as biomarker for acute kidney injury (Lorenzen et al. 2011, Clin J Am Soc Nephrol 6:1540-1546; EP2484779; WO 2011027019). Several circulating miRNAs, including miR-150 in plasma (Vasilescu et al. 2009, PLoS One, 4, e7405), and miR-146a, miR-223, miR-499-5p, miR-122 and miR-193b in serum (Wang et al. 2010, Biochem Biophys Res Commun 394: 184-188; Wang et al. 2012, Journal of Trauma and Acute Care Surgery 73:850-854) are associated with and suggested as biomarker for sepsis. Concerning a potential diagnostic role of miR-210 in sepsis the art is less elaborate and especially less clear. While Huang et al. (2014, BioMed Research International Article ID 594350) lists miR-210 as a low quality biomarker for sepsis, Lorenzen et al. (2011, Clin J Am Soc Nephrol 6:1540-1546) demonstrated that there is no significant difference in levels of circulating miR-210 in patients with or without sepsis. Similarly, for therapeutic effects in osteoarthritis, Zhang et al. (2015 Scientific Reports 5:12775) reported that in chondrocytes miR-210 was inhibited upon LPS treatment and that a miR-210 mimic reduced LPS-induced pro-inflammatory cytokines production. Also Qi et al. (2012 FEBS Letters 586:1201-1207) teaches that transfection of miR-210 mimics significantly inhibit LPS-induced production of inflammatory cytokines, while transfection of anti-miR-210 inhibitors increased LPS-induced expression of proinflammatory cytokines. However, the results disclosed in the current application reveal an opposite mechanism in macrophages (i.e. miR-210 reduction protects against LPS-induced tissue damage and against LPS induced pro-inflammatory cytokine release) and thus teaches away the results of Zhang et al (2015) and Qi et al (2012). Moreover, to the best of our knowledge, the state of the art is completely silent about the link between miR-210 in macrophages and the treatment of sepsis or *Trypanosoma* infections, let alone the downregulation of miR-210 expression to treat sepsis or *Trypanosoma* infections.

SUMMARY

The application describes the role of miR-210 in inflammatory responses with an M1-like phenotype. Applicants found that the expression level of miR-210 is highly induced upon treatment with M1 cytokines and downregulated upon M2 cytokine treatment. Moreover, reducing the expression level of miR-210 in a genetic and/or pharmaceutical way improved the survival rate of a sepsis mice model as well as that of mice that were infected with *Trypanosoma brucei*. It is thus an aspect of this application to provide an inhibitor of miR-210 for use in the treatment of an inflammatory disease characterized by an M1 macrophage response, wherein said inhibitor is a single-stranded oligonucleotide that hybridizes with miR-210 or is a nuclease that cuts the miR-210 nucleotide sequence. Said nucleotide sequence can be a DNA sequence or an RNA sequence. In a particular embodiment, said inflammatory disease is sepsis or *Trypanosoma* infection. In a more particular embodiment, the miR-210 inhibitor for use in treatment of sepsis, *Trypanosoma* infection or other inflammatory diseases characterized by an M1 macrophage response is selected from an antisense oligomer, a miRNA, a siRNA, a shRNA, a gapmer, an antagomir, a morpholino, a locked nucleic acid, a peptide nucleic acid, a ribozyme, ZFN, a TALEN, a CRISPR-Cas, a CRISPR-C2c2 or a meganuclease. For pharmaceutical purposes said inhibitor should be formulated in a pharmaceutical composition. Therefore, in another embodiment, a pharmaceutical composition comprising said inhibitor of miR-210 is provided for use in treatment of an inflammatory disease characterized by an M1 macrophage response. In a more particular embodiment, said inflammatory disease is sepsis or *Trypanosoma* infection.

Another aspect of the application is a method of treating an inflammatory disease characterized by an M1 macrophage response in a subject in need thereof, said method comprising:
    administering an inhibitor of miR-210 to said subject, wherein said inhibitor is a single-stranded oligonucleotide that hybridizes with miR-210 and/or is a nuclease that cuts the miR-210 nucleotide sequence;
    or administering a pharmaceutical composition to said subject, wherein said pharmaceutical composition comprises said inhibitor of miR-210;
    to treat an inflammatory disease characterized by an M1 macrophage response in said subject.

In one embodiment, said inflammatory disease is sepsis or *Trypanosoma* infection. In another embodiment, said inhibitor is selected from an antisense oligomer, a miRNA, a siRNA, a shRNA, a gapmer, an antagomir, a morpholino, a locked nucleic acid, a peptide nucleic acid, a ribozyme, ZFN, a TALEN, a CRISPR-Cas, a CRISPR-C2c2, a meganuclease.

Yet, another aspect of this application is a screening method to identify a compound for use in treating sepsis or *Trypanosoma* infection, said method comprises:

administering a test compound to eukaryotic cells in an in vitro cell culture set up;

determining the expression and/or activity of miR-210 in said cells and in untreated control cells;

wherein a reduction of miR-210 expression and/or miR-210 activity in treated cells compared to untreated control cells of at least 10% identifies said test compound as a compound for use in treating sepsis or *Trypanosoma* infection.

In one embodiment, a method is provided to produce a pharmaceutical composition comprising a compound, wherein said compound is identified by the above described screening method.

In yet another aspect, a method of diagnosing the presence of and/or risk of developing an inflammatory disease characterized by an M1 macrophage response in a subject, said method comprises determining the expression of miR-210 in said subject and in a healthy control, wherein an increase of said expression of at least 10% in said subject compared to said healthy control, is indicative for said subject to develop or to be at risk of developing an inflammatory disease characterized by an M1 macrophage response. In a more particular embodiment, said inflammatory disease characterized by an M1 macrophage response is sepsis or *Trypanosoma brucei* infection.

DETAILED DESCRIPTION

Definitions

Figure 1:
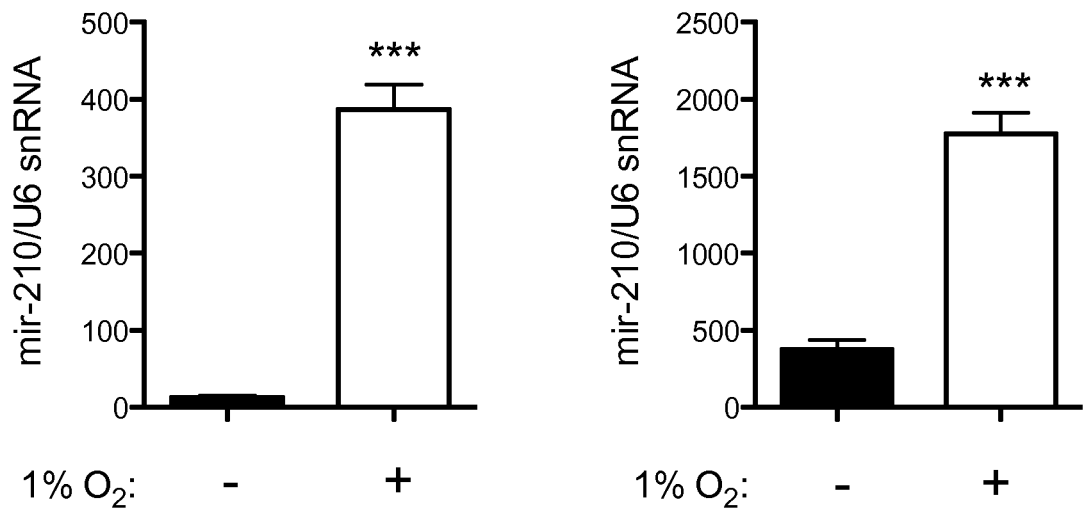
FIG. 1. Hypoxia-induced miR-210 expression in PEMs (left) and in BMDMs (right). The level of miR-210 was normalized using the U6 snRNA levels of the samples. ***$P<0.0005$ FIG. 2. miR-210 expression level is enhanced by M1 cytokines and repressed by M2 cytokines. Levels of miR-210 in untreated PEMs, PEMs treated with LPS or PEMs treated with the M2 cytokine IL-4.

The present invention will be described with respect to particular embodiments and with reference to certain drawings but the invention is not limited thereto but only by the claims. Any reference signs in the claims shall not be construed as limiting the scope. The drawings described are only schematic and are non-limiting. In the drawings, the size of some of the elements may be exaggerated and not drawn on scale for illustrative purposes. Where the term "comprising" is used in the present description and claims, it does not exclude other elements or steps. Where an indefinite or definite article is used when referring to a singular noun e.g. "a" or "an", "the", this includes a plural of that noun unless something else is specifically stated. Furthermore, the terms first, second, third and the like in the description and in the claims, are used for distinguishing between similar elements and not necessarily for describing a sequential or chronological order. It is to be understood that the terms so used are interchangeable under appropriate circumstances and that the embodiments of the invention described herein are capable of operation in other sequences than described or illustrated herein. The following terms or definitions are provided solely to aid in the understanding of the invention. Unless specifically defined herein, all terms used herein have the same meaning as they would to one skilled in the art of the present invention. Practitioners are particularly directed to Sambrook et al., Molecular Cloning: A Laboratory Manual, 4th ed., Cold Spring Harbor Press, Plainsview, N.Y. (2012); and Ausubel et al., current Protocols in Molecular Biology (Supplement 100), John Wiley & Sons, New York (2012), for definitions and terms of the art. The definitions provided herein should not be construed to have a scope less than understood by a person of ordinary skill in the art.

Sepsis is a life-threatening inflammatory disease and there is a high unmet need to develop means and methods to treat subjects which are confronted with this M1-response inflammation. For this purpose, inhibitors of microRNA-210 are provided in this application. MicroRNAs (miRNA or miR) belong to the group of small RNAs. Small RNAs are noncoding RNAs and have the function to guide molecules in different regulatory pathways. They have the characteristics to induce degradation of mRNA—and thus repress translation of target RNA—and they can be divided in two groups by their origin. The first class contains small interfering RNAs (siRNAs), which are generated from long double stranded RNA. siRNAs can be classified in 3 sub-groups: transacting siRNA, repeat-associated siRNA and small scan RNA. The second group small RNAs comprises microRNAs. MicroRNAs are regulators of several biological processes. Genes that are involved in developmental processes have an enrichment of miRNA binding sites, thus cell growth and cellular differentiation are under strong regulation of miRNAs. Genes involved in pathology and physiology are also under regulation of miRNAs. In this application Applicant describes the surprising role of miR-210 in inflammatory diseases that are characterized by an M1 macrophage response.

In a first aspect, the application provides an inhibitor of miR-210 for use in treatment of an inflammatory disease characterized by an M1 macrophage response, wherein said inhibitor is a single-stranded oligonucleotide that hybridizes with miR-210 or is a nuclease that cuts the miR-210 nucleotide sequence. More particularly said inflammatory disease is selected from sepsis or *Trypanosoma* infection. Thus in one embodiment, the application provides an inhibitor of miR-210 for use in treatment of sepsis, wherein said inhibitor is a single-stranded oligonucleotide that hybridizes with miR-210 or is a nuclease that cuts the miR-210 nucleotide sequence. In another embodiment, the application provides an inhibitor of miR-210 for use in treatment of *Trypanosoma* infection, more particularly *T. brucei* infection, wherein said inhibitor is a single-stranded oligonucleotide that hybridizes with miR-210 or is a nuclease that cuts the miR-210 nucleotide sequence.

The term "microRNA", "miRNA" or "miR" is used herein to refer to short (typically 20-24 nt) non-coding RNAs that are involved in post-transcriptional regulation of gene expression in multicellular organisms by affecting both the stability and translation of messenger RNAs (mRNAs) (Ha and Kim 2014 Nature Reviews Molecular Cell Biology 15:509-524 and references therein). miRNAs thus act as guide molecules in RNA silencing. They are involved in nearly all developmental and pathological processes in animals. "miR-210", "MIR210" or "microRNA 210" as used herein refers to the microRNA 210 gene (in humans, also indicated as "hsa-mir-210" or "mir-210" or "MIRN210", characterized by HGNC ID: 31587; Gene ID: 406992; MIMID: 612982; miRBase MI0000286; in mice ("mmu-mir-210"): GeneID: 387206; miRBase MI0000695)). The pre-miR-210 sequence comprises two mature miR-210 sequences, i.e. miR210-5p (of which the sequence is depicted in SEQ ID No. 2) and miR210-3p (of which the sequence is depicted in SEQ ID No. 3). In particular embodiments, miR210 is the nucleic acid molecule depicted in SEQ ID No. 2 or SEQ ID No. 3. The nucleic acid sequence of pre-miR210 is depicted in SEQ ID No.1.

The biogenesis of miRNAs is under tight temporal and spatial control, and their dysregulation is associated with many human diseases, particularly cancer. First, miRNAs are transcribed by RNA polymerase II as part of capped and polyadenylated primary transcripts (pri-miRNAs) that can be either protein-coding or non-coding. The subsequent miRNA biogenesis is regulated at multiple levels. First, following transcription, the primary miRNA (pri-miRNA) undergoes several steps of maturation (Ha and Kim 2014, Nature Reviews Molecular Cell Biology 15:509-524). The pri-miRNA is long (typically over 1 kb) and contains a local stem-loop structure, in which mature miRNA sequences are embedded. A typical pri-miRNA consists of a stem of 33-35 bp, a terminal loop and single-stranded RNA segments at both the 5' and 3' sides (Ha and Kim 2014, Nature Reviews Molecular Cell Biology 15:509-524). The microprocessor complex comprising the nuclear RNase III Drosha and the cofactor DGCR8 initiates the maturation process by cropping the stem-loop to release a stem-loop precursor miRNA (pre-miRNA), which is a small hairpin-shaped RNA of ~30 approximately 70 nucleotides in length. The efficiency of the microprocessor complex is crucial for determining the miRNA abundance. Following the microprocessor complex activity, the pre-miRNA is exported into the cytoplasm where maturation can be completed. pre-miRNA is cleaved by the cytoplasmic Dicer ribonuclease, liberating a small RNA duplex. When two mature microRNAs originate from opposite arms of the same pre-miRNA and are found in roughly similar amounts, they are denoted with a −3p or −5p suffix. The mature (single-stranded) miRNAs are then incorporated into a RNA-induced silencing complex (RISC), which recognizes target mRNAs through imperfect base pairing with the miRNA and most commonly results in translational inhibition or destabilization of the target mRNA. Typically, miRNAs bind complementary sequences in the 3'-UTRs of target mRNAs to induce nucleolytic degradation or inhibit translation. Additionally, also non-canonical pathways for miRNA biogenesis, including those that are independent of Drosha or Dicer, are emerging.

"Inhibitor of miR-210" as used herein refers to molecules that interfere with the function of miR-210, i.e. expression of miR-210 and/or activity of miR-210. Given that miR-210 originates from pre-miR-210 and pri-miR-210, an "inhibitor of miR-210" can also be an inhibitor of pre-miR-210 or pri-miR-210. The inhibition can be done either at the DNA level (e.g. by interfering with transcription of a functional pri-miRNA-210) or at the RNA level (e.g. by interfering with the successive miRNA biogenesis steps, through destabilization of the pri-miRNA-210 or derivatives thereof such as pre-miR-210 so that they are degraded, or typically in case of noncoding RNAs, by interfering with the miRNA itself, e.g. through hybridization). The "inhibitor of miR-210" disclosed in this application can thus be an "inhibitor of miR-210 expression" or an "inhibitor of miR-210 activity". Said "inhibitor of miR-210 expression" refers to a molecule that negatively affects the formation of the mature miR-210, thus from miR-210 transcription to biogenesis, while said "inhibitor of miR-210 activity" refers to a molecule that negatively affects the function of the mature miR-210 (e.g. by preventing the miR-210 to bind to its target).

Inhibiting miR-210 at the DNA level can for instance be done by inhibiting functional expression of the miR-210 gene itself. With "functional expression" of the miR-210 gene, it is meant the transcription of functional miR-210 gene product. "Inhibition of functional expression" at the DNA level can e.g. be achieved by removing or disrupting the miR-210 gene, or preventing transcription to take place (in both instances preventing synthesis of the first miR-210 gene product, i.e. pri-miR-210). If inhibition is to be achieved at the DNA level, this may be done using gene therapy to knock-out or disrupt the miR-210 gene. As used herein, a "knock-out" can be a gene knockdown or the gene can be knocked out by a mutation such as, a point mutation, an insertion, a deletion, a frameshift, or a missense mutation by techniques known in the art, including, but not limited to, retroviral gene transfer. The lack of transcription can e.g. be caused by epigenetic changes (e.g. DNA methylation) or by loss-of-function mutations. A "loss-of-function" or "LOF" mutation as used herein is a mutation that prevents, reduces or abolishes the function of a gene product as opposed to a gain-of-function mutation that confers enhanced or new activity on a protein. LOF can be caused by a wide range of mutation types, including, but not limited to, a deletion of the entire gene or part of the gene, splice site mutations, frame-shift mutations caused by small insertions and deletions, nonsense mutations, missense mutations replacing an essential amino acid and mutations preventing correct cellular localization of the product. Also included within this definition are mutations in promoters or regulatory regions of miR-210 if these interfere with transcription. Some miRNA genes (intronic miRNAs) reside in the introns of protein-coding genes and, thus, share the promoter of the host gene. Moreover it has been noted that miRNA genes often have multiple transcription start sites and that the promoters of intronic miRNAs are sometimes distinct from the promoters of their host genes (Ha and Kim 2014, Nature Reviews Molecular Cell Biology 15:509-524). A null mutation is an LOF mutation that completely abolishes the function of the gene product. A null mutation in one allele will typically reduce expression levels by 50%, but may have severe effects on the function of the gene product.

Another way in which genes can be knocked out is by the use of nucleases, such as zinc-finger nucleases (ZFNs), Transcription Activator-Like Effector Nucleases (TALENs), meganucleases or CRISPR-Cas. "Nucleases" as used herein are enzymes that cut nucleotide sequences. These nucleotide sequences can be DNA or RNA. If the nuclease cleaves DNA, the nuclease is also called a DNase. If the nuclease cuts RNA, the nuclease is also called an RNase.

ZFN are artificial restriction enzymes generated by fusing a zinc finger DNA-binding domain to a DNA-cleavage domain. Zinc finger domains can be engineered to target desired DNA sequences, which enables zinc-finger nucleases to target a unique sequence within a complex genome. By taking advantage of endogenous DNA repair machinery, these reagents can be used to precisely alter the genomes of higher organisms. Other technologies for genome customization that can be used to knock out genes are meganucleases and TAL effector nucleases (TALENs, Cellectis bioresearch). A TALEN® is composed of a TALE DNA binding domain for sequence-specific recognition fused to the catalytic domain of an endonuclease that introduces double strand breaks (DSB). The DNA binding domain of a TALEN® is capable of targeting with high precision a large recognition site (for instance 17 bp). Meganucleases are sequence-specific endonucleases, naturally occurring "DNA scissors", originating from a variety of single-celled organisms such as bacteria, yeast, algae and some plant organelles. Meganucleases have long recognition sites of between 12 and 30 base pairs. The recognition site of natural meganucleases can be modified in order to target native genomic DNA sequences (such as endogenous genes). Another recent genome editing technology is the CRISPR-Cas system, which can be used to achieve RNA-guided genome engineering. CRISPR interference is a genetic technique which allows for sequence-specific control of gene expression in prokaryotic and eukaryotic cells. It is based on the bacterial immune system-derived CRISPR (clustered regularly interspaced palindromic repeats) pathway.

Second, miR-210 can be inhibited at the level of RNA. This can for example be done by the inhibitory RNA technology wherein inhibitors will break down transcribed pri-miR or derivatives along the miRNA biogenesis process. The inhibitory RNA technology or RNA interference (RNAi) is a form of post-transcriptional gene silencing that is used in this application as one of the methods to inhibit or reduce the functional expression of miR-210. The phenomenon of RNA interference was first observed and described in *Caenorhabditis elegans* where exogenous double-stranded RNA (dsRNA) was shown to specifically and potently disrupt the activity of genes containing homologous sequences through a mechanism that induces rapid degradation of the target RNA. Numerous reports have describe the same catalytic phenomenon in other organisms, including experiments demonstrating spatial and/or temporal control of gene inactivation, including plants, protozoa, invertebrates, vertebrates and mammals. RNAi mediated degradation of the target mRNA can be detected by measuring levels of the target mRNA or protein in the cells of a subject, using standard techniques for isolating and quantifying mRNA or protein as described in this application. The mediators of sequence-specific messenger RNA degradation are small interfering RNAs (siRNAs) generated by ribonuclease III cleavage from longer dsRNAs. Generally, the length of siRNAs is between 20-25 nucleotides (Elbashir et al. (2001) Nature 411, 494 498). The siRNA typically comprise a sense RNA strand and a complementary antisense RNA strand annealed together by standard Watson Crick base pairing interactions (hereinafter "base paired"). The sense strand comprises a nucleic acid sequence that is identical to a target sequence (i.e. the miR-210 sequence in this application) contained within the target mRNA. The sense and antisense strands of the present siRNA can comprise two complementary, single stranded RNA molecules or can comprise a single molecule in which two complementary portions are base paired and are covalently linked by a single stranded "hairpin" area (often referred to as shRNA). The siRNAs that can be used to inhibit or reduce the functional expression of miR-210 can comprise partially purified RNA, substantially pure RNA, synthetic RNA, or recombinantly produced RNA, as well as altered RNA that differs from naturally occurring RNA by the addition, deletion, substitution and/or alteration of one or more nucleotides. Such alterations can include addition of non-nucleotide material, such as to the end(s) of the siRNA or to one or more internal nucleotides of the siRNA, including modifications that make the siRNA resistant to nuclease digestion. The siRNAs can be targeted to any stretch of approximately 19 to 25 contiguous nucleotides in miR-210 sequence (the "target sequence"). Techniques for selecting target sequences for siRNA are well known in the art. Thus, the sense strand of the present siRNA comprises a nucleotide sequence identical to any contiguous stretch of about 19 to about 25 nucleotides in the target mRNA. siRNAs can be obtained using a number of techniques known to those of skill in the art. For example, the siRNAs can be chemically synthesized or recombinantly produced using methods known in the art. Preferably, the siRNA of the invention are chemically synthesized using appropriately protected ribonucleoside phosphoramidites and a conventional DNA/RNA synthesizer. The siRNA can be synthesized as two separate, complementary RNA molecules, or as a single RNA molecule with two complementary regions. Commercial suppliers of synthetic RNA molecules or synthesis reagents include Proligo (Hamburg, Germany), Dharmacon Research (Lafayette, Colo., USA), Pierce Chemical (part of Perbio Science, Rockford, Ill., USA), Glen Research (Sterling, Va., USA), ChemGenes (Ashland, Mass., USA) and Cruachem (Glasgow, UK). Alternatively, siRNA can also be expressed from recombinant circular or linear DNA plasmids using any suitable promoter. Suitable promoters for expressing siRNA targeted against miR-210 activity from a plasmid include, for example, the U6 or H1 RNA pol III promoter sequences and the cytomegalovirus promoter. Selection of other suitable promoters is within the skill in the art. The recombinant plasmids of the invention can also comprise inducible or regulatable promoters for expression of the siRNA in a particular tissue or in a particular intracellular environment. The siRNA expressed from recombinant plasmids can either be isolated from cultured cell expression systems by standard techniques, or can be expressed intracellularly, e.g. in brain tissue or in neurons. siRNAs can also be expressed intracellularly from recombinant viral vectors. The recombinant viral vectors comprise sequences encoding the siRNAs of the invention and any suitable promoter for expressing the siRNA sequences. The siRNA will be administered in an "effective amount" which is an amount sufficient to cause RNAi mediated degradation of the target mRNA, or an amount sufficient to inhibit the cellular TAG lipid storage level. One skilled in the art can readily determine an effective amount of the siRNA of the invention to be administered to a given subject, by taking into account factors such as involuntary muscle contraction; the extent of the disease penetration; the age, health and sex of the subject; the route of administration; and whether the administration is regional or systemic. Generally, an effective amount of siRNAs targeting miR-210 expression comprises an intracellular concentration of from about 1 nanomolar (nM) to about 100 nM, preferably from about 2 nM to about 50 nM, more preferably from about 2.5 nM to about 10 nM. It is contemplated that greater or lesser amounts of siRNA can be administered.

Next to the use of dsRNA or the derived siRNAs, also antisense oligomers can be used as inhibitors of miR-210 expression. An "antisense oligomer" refers to an antisense molecule or anti-gene agent that comprises an oligomer of at least about 10 nucleotides in length. In particular embodiments an antisense oligomer comprises at least 15, 18, 20, 25, 30, 35, 40, or 50 nucleotides. Antisense approaches involve the design of oligonucleotides (either DNA or RNA, or derivatives thereof) that are complementary to the miRNA of choice, particularly miR-210. Antisense RNA may be introduced into a cell to inhibit translation of a complementary mRNA by base pairing to it and physically obstructing the translation machinery. This effect is therefore stoichiometric. Absolute complementarity, although preferred, is not required. A sequence "complementary" to a portion of an RNA, as referred to herein, means a sequence having sufficient complementarity to be able to hybridize with the RNA, forming a stable duplex; in the case of double stranded antisense polynucleotide sequences, a single strand of the duplex DNA may thus be tested, or triplex formation may be assayed. The ability to hybridize will depend on both the degree of complementarity and the length of the antisense polynucleotide sequence. Generally, the longer the hybridizing polynucleotide sequence, the more base mismatches with an RNA it may contain and still form a stable duplex (or triplex, as the case may be). One skilled in the art can ascertain a tolerable degree of mismatch by use of standard procedures to determine the melting point of the hybridized complex.

An antisense construct can be delivered, for example, as an expression plasmid, which, when transcribed in the cell, produces RNA that is complementary to at least a unique portion of miR-210.

Besides specifically targeting pri-miR-210, pre-miR-210, miR-210 or any other RNA derivatives of the miR-210 gene, an inhibitor of miR-210 expression can also affect components of the miRNA biogenesis process. As described above, regulation of miRNA biogenesis is a complex process and any aberration at the level of miRNA processing—starting from the pri-miRNA210 and ending with the production of mature single stranded miRNA210—will affect the expression of miR-210. Thus concerning this application, molecules or mechanisms that inhibit the action of Drosha and Dicer in the nucleus and cytoplasm or negatively affect miRNA modification by RNA editing, RNA methylation, uridylation and adenylation but also Argonaute loading and RNA decay are all considered as inhibitors of miR-210 expression.

A third way of inhibiting miR-210 expression can for example be by destabilization of the miR-210 (e.g. by UTR variants) so that miR-210 is degraded before it can regulate its target, for example by lack of efficient folding of the miRNA.

Inhibiting miR-210 activity is done by inhibiting, preventing or reducing hybridisation of miR-210 with its target sequence. This can be measured in a quantitative way by analysing the expression level of the target of miR-210 before and after adding the inhibitor of miR-210. An enhanced expression of the target of miR-210 is indicative for an inhibited miR-210 activity. Examples of such miRNA210 inhibitors are miRNA inhibitor molecules that are between 17 and 25 nucleotides in length and comprise a 5' to 3' sequence that is at least 90% complementary to the 5' to 3' sequence of a mature miRNA (particularly of miR-210). These antisense oligomers used to inhibit miR function may consist of DNA, RNA or other, synthetic structures such as phosphorothiates, 2'-O-alkyl ribonucleotide chimeras, locked nucleic acid (LNA) (which will be discussed further), peptide nucleic acid (PNA), or morpholinos. With the exception of RNA oligomers, PNAs and morpholinos, antisense oligomers typically act in eukaryotic cells through the mechanism of RNase H-mediated target cleavage. PNAs and morpholinos bind complementary DNA and RNA targets with high affinity and specificity, and thus act through a simple steric blockade of the RNA translational machinery or of miRNA binding to its target, and appear to be completely resistant to nuclease attack. Recently it has been shown that morpholino antisense oligonucleotides in zebrafish and frogs overcome the limitations of RNase H-competent antisense oligonucleotides, which include numerous non-specific effects due to the non-target-specific cleavage of other mRNA molecules caused by the low stringency requirements of RNase H. Morpholino oligomers therefore represent an important new class of antisense molecule. Oligomers of the invention may be synthesized by standard methods known in the art. As examples, phosphorothioate oligomers may be synthesized by the method of Stein et al. (1988) 20 Nucleic Acids Res. 16, 3209 3021), methylphosphonate oligomers can be prepared by use of controlled pore glass polymer supports (Sarin et al. (1988) Proc. Natl. Acad. Sci. USA. 85, 7448-7451). Morpholino oligomers may be synthesized by the method of Summerton and Weller U.S. Pat. Nos. 5,217,866 and 5,185,444.

Another particularly form of antisense RNA strategy are gapmers. A gapmer is a chimeric antisense oligonucleotide that contains a central block of deoxynucleotide monomers sufficiently long to induce RNase H cleavage. The central block of a gapmer is flanked by blocks of 2'-O modified ribonucleotides or other artificially modified ribonucleotide monomers such as bridged nucleic acids (BNAs) that protect the internal block from nuclease degradation. Gapmers have been used to obtain RNase-H mediated cleavage of target RNAs, while reducing the number of phosphorothioate linkages. Phosphorothioates possess increased resistance to nucleases compared to unmodified DNA. However, they have several disadvantages. These include low binding capacity to complementary nucleic acids and non-specific binding to proteins that cause toxic side-effects limiting their applications. The occurrence of toxic side-effects together with non-specific binding causing off-target effects has stimulated the design of new artificial nucleic acids for the development of modified oligonucleotides that provide efficient and specific antisense activity in vivo without exhibiting toxic side-effects. By recruiting RNase H, gapmers selectively cleave the targeted oligonucleotide strand. The cleavage of this strand initiates an antisense effect. This approach has proven to be a powerful method in the inhibition of gene functions and is emerging as a popular approach for antisense therapeutics. Gapmers are offered commercially, e.g. LNA longRNA GapmeRs by Exiqon, or MOE gapmers by Isis pharmaceuticals. MOE gapmers or "2'MOE gapmers" are an antisense phosphorothioate oligonucleotide of 15-30 nucleotides wherein all of the backbone linkages are modified by adding a sulfur at the non-bridging oxygen (phosphorothioate) and a stretch of at least 10 consecutive nucleotides remain unmodified (deoxy sugars) and the remaining nucleotides contain an O'-methyl O'-ethyl substitution at the 2' position (MOE).

Particularly envisaged molecules for inhibition of miRNAs are antagomirs. Antagomirs are chemically engineered oligonucleotides that can be used to silence endogenous microRNA. An antagomir is a small synthetic RNA that is perfectly complementary to the specific miRNA target with either mispairing at the cleavage site of Ago2 or some sort of base modification to inhibit Ago2 cleavage. Usually, antagomirs have some sort of modification to make it more resistant to degradation. Without being bound to a particular mechanism, it is believed that antagomirization (the process by which an antagomir inhibits miRNA activity) operates by irreversibly binding the miRNA.

Finally, miRNA activity may also be inhibited using ribozymes instead of antisense RNA. Ribozymes are catalytic RNA molecules with enzyme-like cleavage properties that can be designed to target specific RNA sequences. Successful target gene inactivation, including temporally and tissue-specific gene inactivation, using ribozymes has been reported in mouse, zebrafish and fruitflies. The feasibility of this approach for miRNA modulation has recently been demonstrated (Suryawanshi H et al., Mol Biosyst. 6(10): 1807-9 (2010)). Recently, it was demonstrated that the Crispr-Cas editing system can also be used to target RNA. It has been shown that the Class 2 type VI-A CRISPR-Cas effector C2c2 can be programmed to cleave single stranded RNA targets carrying complementary protospacers (Abudayyet et al 2016 Science 10.1126/science.aaf5573). C2c2 is a single-effector endoRNase mediating ssRNA cleavage once it has been guided by a single crRNA guide toward the target RNA. This system can thus also be used, once a functional miR-210 is produced in the cell, to target and thus to break down miR-210.

Thus, the inhibitor envisaged to inhibit miR-210 expression is an inhibitor from the inhibitory RNA technology (e.g. an antisense oligomer, a shRNA, a miRNA); or is a nuclease with DNase activity that obtained sequence specificity from a guiding RNA in case of CRISPR or from a guiding DNA-binding protein in case of ZFN, TALEN or mega nuclease. The inhibitor envisaged to inhibit miR-210 activity is an inhibitor that hybridizes with miR-210 (such as a gapmer, an antagomir, a morpholino) or is a nuclease with RNase activity that breaks down miR-210 (e.g. CRISPR-C2c2, ribozyme).

Therefore, in another embodiment, the application provides an inhibitor of miR-210 for use in treatment of an inflammatory disease characterized by an M1 macrophage response, wherein said inhibitor is selected from the list consisting of an antisense oligomer, a miRNA, a siRNA, a shRNA, a gapmer, an antagomir, a morpholino, a locked nucleic acid, a peptide nucleic acid, a ribozyme, ZFN, a TALEN, a CRISPR-Cas, a CRISPR-C2c2 and a meganuclease. In a more particular embodiment, the application provides an inhibitor of miR-210 for use in treatment of sepsis or *Trypanosoma* infection, wherein said inhibitor is selected from the list consisting of an antisense oligomer, a miRNA, a siRNA, a shRNA, a gapmer, an antagomir, a morpholino, a locked nucleic acid, a peptide nucleic acid, a ribozyme, ZFN, a TALE N, a CRISPR-Cas, a CRISPR-C2c2 and a meganuclease.

In another embodiment, the application provides an inhibitor of miR-210 expression and/or miR-210 activity for use in treatment of sepsis, *Trypanosoma* infection or any other inflammatory disease characterised by an M1 macrophage response, wherein said inhibitor is a single-stranded oligonucleotide that hybridises with miR-210 and is selected from the list consisting of an antisense oligomer, a miRNA, a siRNA, a shRNA, a gapmer, an antagomir, a morpholino, a locked nucleic acid, a peptide nucleic acid. In another embodiment, the application provides an inhibitor of miR-210 expression and/or miR-210 activity for use in treatment of sepsis, *Trypanosoma* infection or any other inflammatory disease characterised by an M1 macrophage response, wherein said inhibitor is a nuclease that cleaves the miR-210 encoding DNA sequence or the miR-210 RNA sequence and wherein said inhibitor is selected from the list consisting of a ribozyme, ZFN, a TALEN, a CRISPR-Cas, a CRISPR-C2c2 and a meganuclease. In particular embodiments, said *Trypanosoma* infection is *T. brucei* infection.

In a most particular embodiment of this application, said inhibitor of miR-210 expression and/or activity is a single stranded nucleic acid molecule comprising a 5' to 3' sequence that is at least 90%, at least 91%, at least 92%, at least 93%, at least 94%, at least 95%, at least 96%, at least 97%, at least 98%, at least 99% complementary to the 5' to 3' sequence depicted in SEQ ID No. 2 or 3. In an even more particular embodiment, said inhibitor is a nucleic acid molecule with at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence homology to SEQ ID No. 4.

The term "sequence identity" or "sequence homology" as used herein refers to the extent that sequences are identical on a nucleic acid by nucleic acid basis over a window of comparison. Thus, a "percentage of sequence homology" is calculated by comparing two optimally aligned sequences over the window of comparison, determining the number of positions at which the identical nucleic acid occurs in both sequences to yield the number of matched positions, dividing the number of matched positions by the total number of positions in the window of comparison (i.e., the window size), and multiplying the result by 100 to yield the percentage of sequence identity. A gap, i.e., a position in an alignment where a residue is present in one sequence but not in the other is regarded as a position with non-identical residues. Determining the percentage of sequence homology can be done manually, or by making use of computer programs that are available in the art. Examples of useful algorithms are PILEUP (Higgins & Sharp, CABIOS 5:151 (1989), BLAST and BLAST 2.0 (Altschul et al. J. Mol. Biol. 215: 403 (1990). Software for performing BLAST analyses is publicly available through the National Center for Biotechnology Information (ncbi.nlm.nih.gov). In particular embodiments, the window of comparison to determine the sequence identity of miR-210 and another nucleic acid sequence is the full length miR-210 sequence.

In the present application it is essential that miR-210 is inhibited (in other words that the functional expression and/or activity of miR-210 is inhibited) in order to have a positive effect on the treatment of inflammatory diseases characterised with an M1-like response, more particularly sepsis or *T. brucei* infection. The inhibition of the functional expression of miR-210 is preferably at least 30%, at least 40%, at least 50%, at least 60%, at least 70%, at least 80%, at least 90%, at least 95% or even 100%. 100% means that no detectable functional expression of miR-210 is detected.

This can be easily analysed with standard techniques known to the person skilled in the art. Non-limiting examples of such techniques are quantitative real-time PCR (Q-RT-PCR) or semi-quantitatively using Northern blotting. However, the nature of the inhibitor and how the effect is achieved by administering the inhibitor is not vital to the invention, as long as the inhibitor inhibits the functional expression and/or activity of miR-210.

"Inflammatory diseases characterized by an M1 macrophage response" as used herein refers to an infection in which M1 macrophages are involved in contrast to inflammatory diseases characterized by an M2 macrophage response.

Generally, M1 macrophages will trigger a decision to fight (e.g. in response to an invading pathogen) while M2 macrophages will repair (e.g. damaged tissue). M1 macrophages respond to IFN-γ (interferon gamma), LPS and/or granulocyte macrophage colony-stimulating factor (GM-CSF), while the group of M2 stimuli comprises IL-4, IL-13, glucocorticoids, IL-10, TGF-β (Martinez and Gordon 2014, F1000Prime Reports 6:13). An M1-type response is mediated by macrophages preferentially producing NO (Nitric Oxide) that inhibits cell proliferation and causes tissue damage, while an M2-type produces ornithine that promotes proliferation and repair (through polyamines and collagen) (Mills 2012, Critical Reviews in Immunology 32:463-488 and references therein). The clearest and most functional way to categorize opposing macrophage activities in innate immunity is the production of NO or ornithine production (Mills 2012, Critical Reviews in Immunology 32:463-488), with NO as best indicator of M1 responses and ornithine production as best indicator of M2 responses. Measuring NO and ornithine production is performed by standard analyses that are well known to the person skilled in the art. One might alternatively measure iNOS or arginase enzyme activities, or the genes that code for it as an indicator for M1 or M2 respectively. Besides NO and ornithine production, other molecules that polarized macrophages produce biochemically define M1 and M2 phenotypes to perform diametrically opposed functions. Indeed, the names M1 and M2 were chosen because M1 and M2 macrophages stimulate T cells to make Th1 or Th2 dominant cytokine responses, respectively. Interestingly, products of M1 and M2 responses mutually inhibit each other. An M1 phenotype (or in other words an M1 type response) leads to the production of one or more molecules selected from the list consisting of IL-1β, TNFα (tumor necrosis factor alpha), IL-7R, CCL2, CCR7, INF-γ, IL-12 and IL-23 (Martinez and Gordon 2014, F1000Prime Reports 6:13). These molecules can thus be evaluated as M1 phenotype markers. Since M1 and Th1 often work in concert to produce characteristic immune responses and disease pathologies, an M1 type response is also referred to in the art as Immune Type 1. In line with this an M2/Th2 response is then referred to as Immune Type 2 (Mills 2012, Critical Reviews in Immunology 32:463-488). For this tissue repair mechanism, ornithine, EGF, VEGF, and other growth factors are produced. Also, wound signals such as TGF-β and adenosine (from fibroblasts and other cells) are important in maintaining M2 activity. Although, a more comprehensive classification for M1/M2 responses is required, it is clear that at present, the M1/M2 paradigm provides a useful framework, especially for selected immune responses. Macrophage activation is associated with profound changes in gene expression profiles and exposure to different tissue-derived stimuli induces distinct polarization profiles, associated with the expression of selected molecules (Mantovani et al 2004, Trends in Immunology 25:677-686). These molecules are not exclusively linked to a certain polarization profile, and polarized macrophages can transform to another polarization status in response to specific stimuli, but based on the art and what is described above, a person skilled in the art is very capable to distinguish inflammatory diseases characterized by an M1 macrophage response from inflammatory diseases characterized by an M2 macrophage response or the skilled one can easily perform standard experiments to know whether an infection depends on an M1 or M2 response based on the current knowledge.

In yet another embodiment, a pharmaceutical composition is provided wherein said composition comprises an inhibitor of miR-210 expression and/or miR-210 activity, wherein said inhibitor is a single-stranded oligonucleotide that hybridizes with miR-210 or is a nuclease that cleaves the miR-210 nucleotide sequence. In a more particular embodiment, said single-stranded oligonucleotide that hybridizes with miR-210 is selected from an antisense oligomer, a miRNA, a siRNA, a shRNA, a gapmer, an antagomir, a morpholino, a locked nucleic acid, a peptide nucleic acid. In another more particular embodiment, said nuclease that cleaves the miR-210 nucleotide sequence is selected from a ribozyme, ZFN, a TALEN, a CRISPR-Cas, a CRISPR-C2c2, a meganuclease.

In another embodiment, a pharmaceutical composition is provided for use in treatment of an inflammatory disease characterizes by an M1 macrophage response, wherein said composition comprises an inhibitor of miR-210 expression and/or miR-210 activity, wherein said inhibitor is a single-stranded oligonucleotide that hybridizes with miR-210 or is a nuclease that cleaves the miR-210 nucleotide sequence. In a more particular embodiment, said single-stranded oligonucleotide that hybridizes with miR-210 is selected from an antisense oligomer, a miRNA, a siRNA, a shRNA, a gapmer, an antagomir, a morpholino, a locked nucleic acid, a peptide nucleic acid. In another more particular embodiment, said nuclease that cleaves the miR-210 nucleotide sequence is selected from a ribozyme, ZFN, a TALEN, a CRISPR-Cas, a CRISPR-C2c2, a meganuclease. In even particular embodiments, said pharmaceutical composition is provided for use in treatment of an inflammatory disease selected from sepsis and T. brucei infection.

The pharmaceutical compositions containing functional inhibitors of miR-210 described herein before can be utilized to achieve the desired pharmacological effect by administration to a patient suffering from sepsis, T. brucei infection or other inflammatory diseases characterized by an M1 macrophage response. A patient, for the purpose of this application, is a mammal, including a human, in need of treatment for sepsis, T. brucei infection or other inflammatory diseases characterized by an M1 macrophage response. Therefore, the present application includes pharmaceutical compositions that are comprised of a pharmaceutically acceptable carrier and a pharmaceutically effective amount of a functional inhibitor of miR-210, or salt thereof. A pharmaceutically acceptable carrier is preferably a carrier that is relatively non-toxic and innocuous to a patient at concentrations consistent with effective activity of the active ingredient so that any side effects ascribable to the carrier do not vitiate the beneficial effects of the active ingredient. A pharmaceutically effective amount of a functional inhibitor of miR-210 is preferably that amount which produces a result or exerts an influence on the particular condition being treated. The compounds of the present application can be administered with pharmaceutically-acceptable carriers well known in the art using any effective conventional dosage unit forms, including immediate, slow and timed release preparations.

The pharmaceutical compositions of this application may also be in the form of oil-in-water emulsions. The emulsions may also contain sweetening and flavoring agents. Oily suspensions may be formulated by suspending the active ingredient in a vegetable oil such as, for example, arachis oil, olive oil, sesame oil or coconut oil, or in a mineral oil such as liquid paraffin. The pharmaceutical compositions may be in the form of sterile injectable aqueous suspensions. Such suspensions may be formulated according to known methods using suitable dispersing or wetting agents and suspending agents, all well-known by the person skilled in the art. The sterile injectable preparation may also be a sterile injectable solution or suspension in a non-toxic parenterally acceptable diluent or solvent. Diluents and solvents that may be employed are, for example, water, Ringer's solution, isotonic sodium chloride solutions and isotonic glucose solutions. In addition, sterile fixed oils are conventionally employed as solvents or suspending media. For this purpose, any bland, fixed oil may be employed including synthetic mono- or diglycerides. In addition, fatty acids such as oleic acid can be used in the preparation of injectables. The compositions of the invention can also contain other conventional pharmaceutically acceptable compounding ingredients, generally referred to as carriers or diluents, as necessary or desired. The nature of additional ingredients and the need of adding those to the composition of the invention is within the knowledge of a skilled person in the relevant art. Conventional procedures for preparing such compositions in appropriate dosage forms can be utilized. Such ingredients and procedures include those described in the following references, each of which is incorporated herein by reference: Powell, M. F. et al., "Compendium of Excipients for Parenteral Formulations" PDA Journal of Pharmaceutical Science & Technology 1998, 52(5), 238-311; Strickley, R. G "Parenteral Formulations of Small Molecule Therapeutics Marketed in the United States (1999)-Part-1" PDA Journal of Pharmaceutical Science & Technology 1999, 53(6), 324-349; and Nema, S. et al., "Excipients and Their Use in Injectable Products" PDA Journal of Pharmaceutical Science & Technology 1997, 51 (4), 166-171.

In yet another embodiment, even though the functional inhibition miR-210 is sufficient to achieve a therapeutic effect, it is likely that stronger, synergistic effects can be obtained in combination with conventional treatment options for sepsis, T. brucei infection and other inflammatory diseases characterized by an M1 macrophage response. The synergistic effect can be obtained through simultaneous, concurrent, separate or sequential use for treating said infections.

In a second aspect, a method is provided to treat an inflammatory disease in a subject in need thereof, wherein said inflammatory disease is characterized by an M1 macrophage response, said method comprising:
  administering an inhibitor of miR-210 to said subject, wherein said inhibitor is a single-stranded oligonucleotide that hybridizes with miR-210 or is a nuclease that cuts the miR-210 nucleotide sequence; or
  administering a pharmaceutical composition to said subject, wherein said pharmaceutical composition comprises a single-stranded oligonucleotide that hybridizes with miR-210 or a nuclease that cuts the miR-210 nucleotide sequence;

to treat an inflammatory disease characterized by an M1 macrophage response in said subject. More particularly, said inflammatory disease characterized by an M1 macrophage response is sepsis or *Trypanosoma* infection, more particularly *T. brucei* infection.

In one embodiment, a method is provided to treat an inflammatory disease in a subject in need thereof, wherein said inflammatory disease is characterized by an M1 macrophage response, said method comprising:
  administering an inhibitor of miR-210 to said subject, wherein said inhibitor is selected from the list consisting of an antisense oligomer, a miRNA, a siRNA, a shRNA, a gapmer, an antagomir, a morpholino, a locked nucleic acid, a peptide nucleic acid, a ribozyme, ZFN, a TALE N, a CRISPR-Cas, a CRISPR-C2c2 and a meganuclease.
  to treat an inflammatory disease characterized by an M1 macrophage response in said subject. In a more particular embodiment, said inflammatory disease characterized by an M1 macrophage response is sepsis or *Trypanosoma* infection.

In another embodiment, a method is provided to treat an inflammatory disease in a subject in need thereof, wherein said inflammatory disease is characterized by an M1 macrophage response, said method comprising:
  administering a pharmaceutical composition to said subject, wherein said pharmaceutical composition comprises an inhibitor of miR-210 selected from the list consisting of an antisense oligomer, a miRNA, a siRNA, a shRNA, a gapmer, an antagomir, a morpholino, a locked nucleic acid, a peptide nucleic acid, a ribozyme, ZFN, a TALEN, a CRISPR-Cas, a CRISPR-C2c2 and a meganuclease;
  to treat an inflammatory disease characterized by an M1 macrophage response in said subject. In a more particular embodiment, said inflammatory disease characterized by an M1 macrophage response is sepsis or *Trypanosoma* infection.

In another embodiment, a method is provided to treat sepsis, said method comprising:
  administering an inhibitor of miR-210 expression and/or miR-210 activity to said subject, wherein said inhibitor is a single-stranded oligonucleotide that hybridizes with miR-210 or is a nuclease that cuts the miR-210 nucleotide sequence; or
  administering a pharmaceutical composition to said subject, wherein said pharmaceutical composition comprises a single-stranded oligonucleotide that hybridizes with miR-210 or a nuclease that cuts the miR-210 nucleotide sequence;
  to treat sepsis in said subject.

In another embodiment, a method is provided to treat *Trypanosoma* infection, said method comprising:
  administering an inhibitor of miR-210 expression and/or miR-210 activity to said subject, wherein said inhibitor is a single-stranded oligonucleotide that hybridizes with miR-210 or is a nuclease that cuts the miR-210 nucleotide sequence; or
  administering a pharmaceutical composition to said subject, wherein said pharmaceutical composition comprises a single-stranded oligonucleotide that hybridizes with miR-210 or a nuclease that cuts the miR-210 nucleotide sequence;
  to treat *Trypanosoma* infection in said subject.

In a particular extension of the second aspect and its accompanying embodiments, said single-stranded oligonucleotide that hybridizes with miR-210 is selected from an antisense oligomer, a miRNA, a siRNA, a shRNA, a gapmer, an antagomir, a morpholino, a locked nucleic acid, a peptide nucleic acid. In a particular extension of the second aspect and its accompanying embodiments, said nuclease that cleaves the miR-210 nucleotide sequence is selected from a ribozyme, ZFN, a TALEN, a CRISPR-Cas, a CRISPR-C2c2, a meganuclease. In particular embodiments, said *Trypanosoma* infection is *T. brucei* infection.

In a third aspect, a screening method is provided to identify a compound for use in treating sepsis or *Trypanosoma* infection, said screening method comprising:
  administering a test compound to eukaryotic cells in an in vitro cell culture set up;
  determining the expression and/or activity of miR-210 in said cells and in untreated control cells;
  wherein a reduction of miR-210 expression and/or miR-210 activity in treated cells of at least 10% compared to untreated control cells identifies said test compound as a compound for use in treating sepsis or *Trypanosoma* infection.

In one embodiment, a screening method is provided to identify a compound for use in treating sepsis or *Trypanosoma* infection, said screening method comprising:
  administering a test compound to eukaryotic cells in an in vitro cell culture set up;
  determining the expression and/or activity of miR-210 in said cells and in untreated control cells;
  wherein a reduction of miR-210 expression and/or miR-210 activity in treated cells of at least 20%, at least 30%, at least 40%, at least 50, at least 60%, at least 70%, at least 80%, at least 90% compared to untreated control cells identifies said test compound as a compound for use in treating sepsis or *Trypanosoma* infection. In particular embodiments, said *Trypanosoma* infection is *T. brucei* infection.

Assay to determine the expression of miR-210 are standard and are known to the person skilled in the art. Briefly and by way of example, expression of genes (including miR-210) can be analyzed using PCR in a quantitative (Q-RT-PCR) or semi-quantitative (RT-PCR) way. Expression can also be analyzed using Northern blotting. Assays to determine the activity of miR-210 are also known to the person skilled in the art. One example of such an assay can be determining the expression of a target gene of miR-210. If the activity of miR-210 is inhibited by a test compound, expression of miR-210's target gene will be inhibited less and thus its expression will increase. Evaluating the difference in expression level of miR-210 target genes before and after adding a test compound can again be done using PCR-based methods or by expressing a fusion protein of the miR-210 target and a reporter protein (e.g. a luminescent protein such as luciferase or a fluorescent protein such as GFP, RFP, . . . ) in an in vitro cell culture. Multiple targets of miR-210 are known to the skilled one. To name a few: E2F3 (Nakada et al 2011, The Journal of Pathology 224: 280-288), FLICE associated huge protein (FLASH)/Caspase-8-associated protein-2 (Casp8ap2) (Kim et al 2009, The Journal of Biological Chemistry 284: 33161-33168), ISCU (iron sulphur cluster homologue) (Chan et al 2009, Cell Metab 10:273-284), activing A receptor type 1B (AcvR1b) (Mizuno et al 2009, FEBS Letters 583:2263-2268), Ephrin-A3 (Fasanaro et al 2008, The Journal of Biological Chemistry 283:15878-15883), glycerol-3-phosphate dehydrogenase 1-like (GPD1L) (Kelly et al 2001, Mol Cell Biol 31: 2696-2706), regulator of differentiation 1 (ROD1) (Fasanaro et al 2012, PlOS One 7: e44651). Also any other nucleotide sequence can be used if that sequence comprises a functional miR-210 binding sequence.

In a fourth aspect, a method is provided to produce a pharmaceutical composition comprising a compound, wherein said compound is identified by a screening method, said screening method comprises the following steps:
- administering a test compound to eukaryotic cells in an in vitro cell culture set up;
- determining the expression and/or activity of miR-210 in said cells and in untreated control cells;
- wherein a reduction of miR-210 expression and/or miR-210 activity in treated cells of at least 10%, at least 20%, at least 30%, at least 40%, at least 50, at least 60%, at least 70%, at least 80%, at least 90% compared to untreated control cells identifies said compound.

The term "compound" is used herein in the context of a "test compound" or a "drug candidate compound" described in connection with the methods of the present invention. As such, these compounds comprise organic or inorganic compounds, derived synthetically or from natural resources. The compounds include polynucleotides, lipids or hormone analogs that are characterized by low molecular weights. Other biopolymeric organic test compounds include small peptides or peptide-like molecules (peptidomimetics) comprising from about 2 to about 40 amino acids and larger polypeptides comprising from about 40 to about 500 amino acids, such as antibodies or antibody conjugates. For high-throughput purposes, compound libraries may be used. Examples include, but are not limited to, natural compound libraries, allosteric compound libraries, peptide libraries, antibody fragment libraries, synthetic compound libraries, etc. In particular embodiments, a compound will "reduce" or "decrease" the expression and/or activity of miR-210 in treated cells. Expression of miR-210 can be easily determined by Q-RT-PCR as in this application, but alternative methods are well-known for the skilled one.

In a fifth aspect, a method of diagnosing the presence of and/or risk of developing an inflammatory disease characterized by an M1 macrophage response in a subject is provided, said method comprises determining the expression of miR-210 in said subject and in a control, wherein an increase of said expression of at least 10%, at least 20%, at least 30%, at least 40%, at least 50%, at least 60%, at least 70%, at least 80%, at least 90% in said subject compared to said control, is indicative for said subject to develop or to be at risk of developing an inflammatory disease characterized by an M1 macrophage response. In a particular embodiment, said inflammatory disease characterized by an M1 macrophage response is sepsis or *Trypanosoma* infection. In particular embodiment, said *Trypanosoma* infection is *T. brucei* infection.

It is to be understood that although particular embodiments, specific configurations as well as materials and/or molecules, have been discussed herein for cells and methods according to the present invention, various changes or modifications in form and detail may be made without departing from the scope and spirit of this invention. The following examples are provided to better illustrate particular embodiments, and they should not be considered limiting the application. The application is limited only by the claims.

EXAMPLES

Example 1: miR-210 is Upregulated in Macrophages by Hypoxia

It has been demonstrated that the expression of miR-210 in hypoxia is upregulated in several cell types (Huang et al. 2010, Trends Mol Med 16:230-237; Wang et al. 2014, Nat Immunol 15:393-401; Chan and Loscalzo 2010, Cell Cycle 9:1072-1083), but up to date there is not a lot known about the role of miR-210 in macrophages. To assess the effect of hypoxia on miR-210 expression in macrophages, the expression of miR-210 in peritoneal macrophages (PEMs) and in bone marrow-derived macrophages (BMDMs) was assessed by qPCR analysis in normoxic and hypoxic (1% $O_2$) conditions. In line with literature, a significant hypoxic induction of miR-210 expression could be observed in PEMs and in BMDMs (FIG. 1).

Example 2. M1 Cytokines Enhance the miR-210 Response

Figure 2:
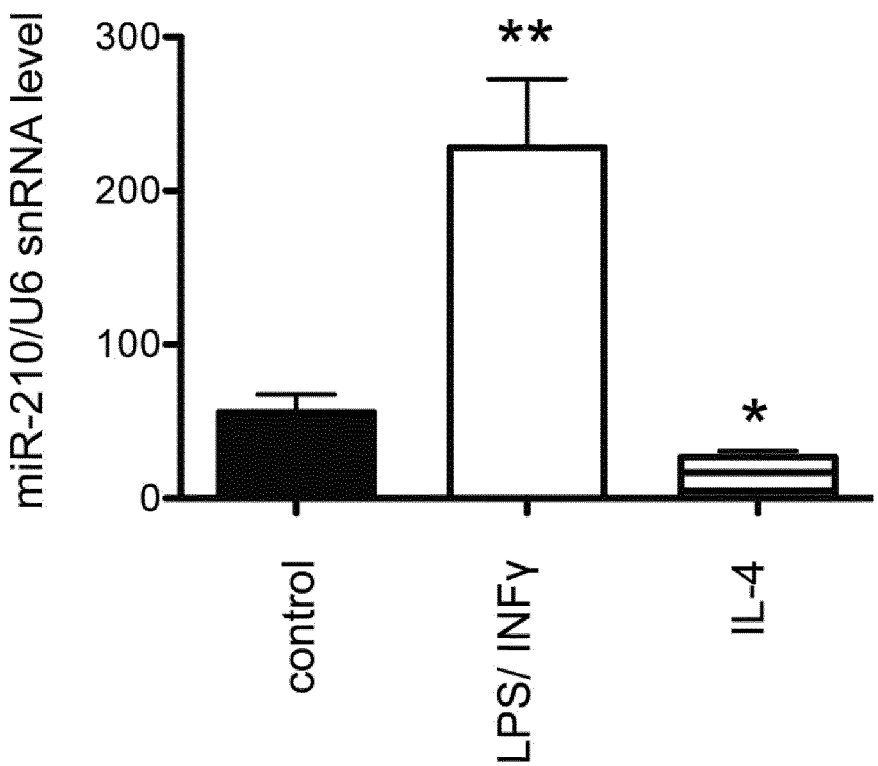

In sepsis, macrophages elicit an M1-like phenotype. Therefore, we investigated the level of miR-210 expression in PEMs stimulated by M1 cytokines. MiR-210 expression was significantly higher in PEMs treated with LPS, which leads to the release of M1 cytokines, compared to the expression level of untreated PEMs (FIG. 2).

Figure 3:
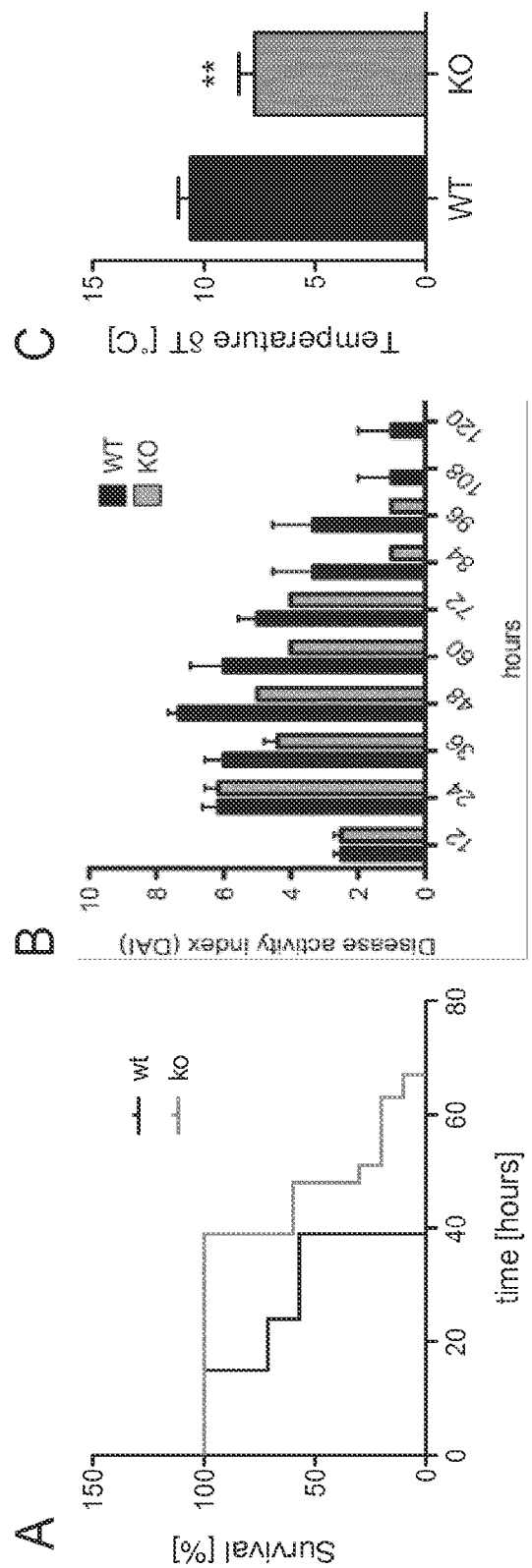
FIG. 3. Loss of miR-210 in the bone marrow leads to better survival in a model of LPS-induced peritonitis. A. LPS (20 mg/kg) injected bone marrow transplanted miR-210 WT or KO mice were continuously monitored for survival. B. DAI of LPS (20 mg/kg) injected miR-210 WT and KO mice was scored every 12 hours to assess a comparison of the clinical symptoms (results are from a different LPS-induced peritonitis in vivo experiment). C. Decrease in temperature after LPS (20 mg/kg) injection in miR-210 WT and KO mice.

Example 3. Survival of LPS-Induced Peritonitis is Better in Mice with Loss of miR-210 in their Bone Marrow To further study the role of miR-210 in M1 polarized macrophages in vivo, we chose a mouse model of sepsis, as macrophages are important mediators in this inflammatory diseases type. The LPS-induced peritonitis model was used to create sepsis in irradiated mice with miR-210 wild-type (WT) or knock-out (KO) bone marrow and a comparison of the survival, the disease activity index (DAI) and decrease in body temperature was performed. The survival of mice with miR-210 KO bone marrow was significantly better than the survival of mice with miR-210 WT bone marrow (FIG. 3). Almost 50% of the WT mice were already dead after 24 hours. At that same time point all the KO mice were still alive. The overall survival of KO mice was substantially prolonged, since all WT mice were dead after 39 hours, whereas all KO mice died within 66 hours after LPS injection (FIG. 3A).

The DAI as readout for the clinical disease symptoms was measured in WT and KO mice at the indicated time points, to further investigate whether the loss of miR-210 in macrophages accelerated the course of LPS-induced peritonitis. The DAI shown in FIG. 3 is from an independent LPS-induced peritonitis experiment than the results of the survival and decrease in temperature. There was no difference in DAI score observed in the first 24 hours after LPS injection between miR-210 WT and KO mice. We observed a higher DAI score in the miR-210 WT mice, upon 36 hours after LPS injection. The combined DAI score over the several hours was significantly higher in the WT compared to the KO mice, reflecting the worse clinical disease symptoms observed in the miR-210 WT mice (FIG. 3B). Decrease in body temperature, which is a typical characteristic of sepsis, was also higher in the WT mice in comparison to the KO mice (FIG. 3C). Upon observation of a better survival, lower DAI and decrease in temperature in miR-210 KO mice, we suggest that the loss of miR-210 in macrophages protects against LPS-induced peritonitis.

Figure 4:
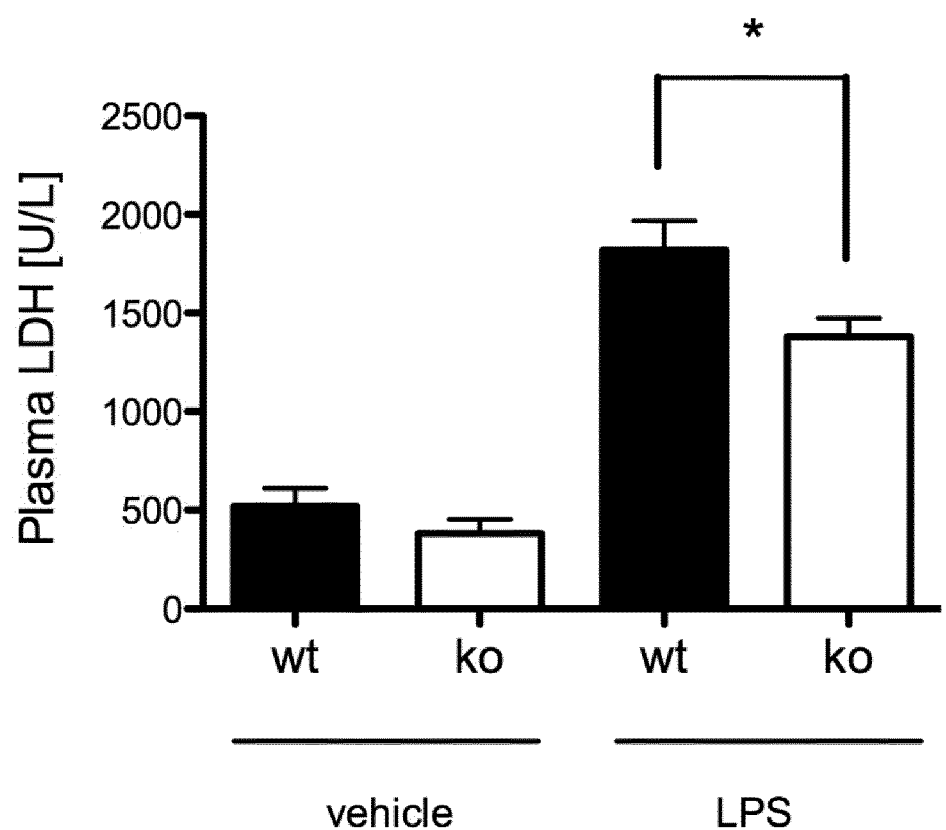
FIG. 4. miR-210 loss in macrophages is protective against LPS-induced organ damage. Blood samples were taken 18 hours after injecting LPS or PBS (vehicle) in miR-210 bone marrow transplanted WT or KO mice and LDH values were measured. *$P<0.05$.
Figure 5:
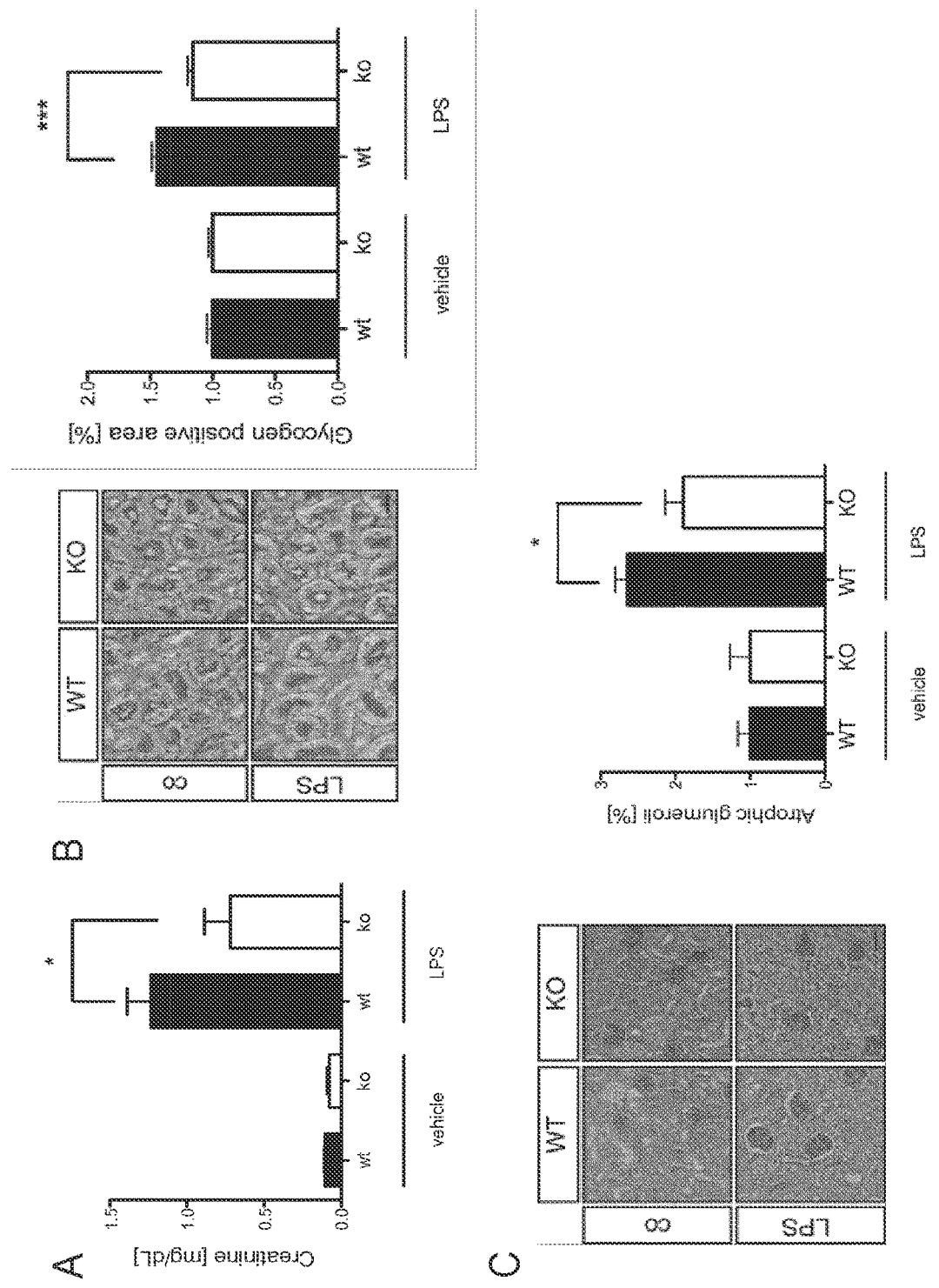
FIG. 5. miR-210 deletion in macrophages is protective against LPS-induced kidney damage. A. Blood samples of miR-210 bone marrow transplanted WT or KO mice were taken 18 hours after injection of LPS (20 mg/kg) or PBS (vehicle) and creatinine levels were quantified. B. Histological PAS staining (left) and analysis of the percentage of glycogen positive area in the kidney tubuli (right) of miR-210 WT or KO mice (indicated with black arrows) 18 hours after LPS (20 mg/kg) or PBS (vehicle) injection. Scale bare, 20 μm. C. H&E staining (left) was performed in kidney sections of miR-210 WT and KO mice treated with LPS or PBS (vehicle) for 18 hours to analyse the percentage of atrophic glumeroli (right). Scale bar, 100 μm. *$P<0.05$ **$P<0.005$.

Example 4. Loss of miR-210 in Macrophages Protects Against LPS-Induced Organ Damage Organ failure is an important characteristic of sepsis and leads frequently to death in humans (Annane et al. 2003, Am J Respir Crit Care Med 168:165-172; Doi et al. 2009, J Clin Invest 119:2868-2878). Thus, the organ damage was measured in miR-210 WT and KO mice treated with LPS in order to further pinpoint the functional role of miR-210 in M1 macrophages. The blood plasma level of LDH, which is used as global marker for inflammation, was significantly higher in miR-210 WT mice treated with LPS compared to the level in miR-210 KO mice treated with LPS (FIG. 4). This implicates more systemic inflammatory processes in LPS treated miR-210 WT mice. The creatinine level (FIG. 5A), the percentage of glycogen positive area in the kidney tubuli (FIG. 5B) and the percentage of atrophic glumeroli (FIG. 5C) were measured to compare kidney damage in miR-210 WT and KO LPS treated mice. These three factors were significantly higher in the miR-210 WT mice treated with LPS compared to the level of these factors in LPS-treated miR-210 KO mice. The high percentage of glycogen positive area in the tubuli of miR-210 WT treated mice indicated higher obstruction of the kidney tubuli. Moreover, hematopoietic miR-210 KO resulted in a reduced number of atrophic glumeroli (FIGS. 5B and C). Blood plasma creatinine levels were measured to determine if these differences in structural damage had an influence on the function of the kidney. The level of creatinine was increased in the treated WT mice as well as in the treated KO mice compared to their controls, but the increase was significantly higher in the treated WT mice compared to treated KO mice (FIG. 5A). So treated WT mice showed a stronger impairment in kidney function in comparison the treated KO mice.

Figure 6:
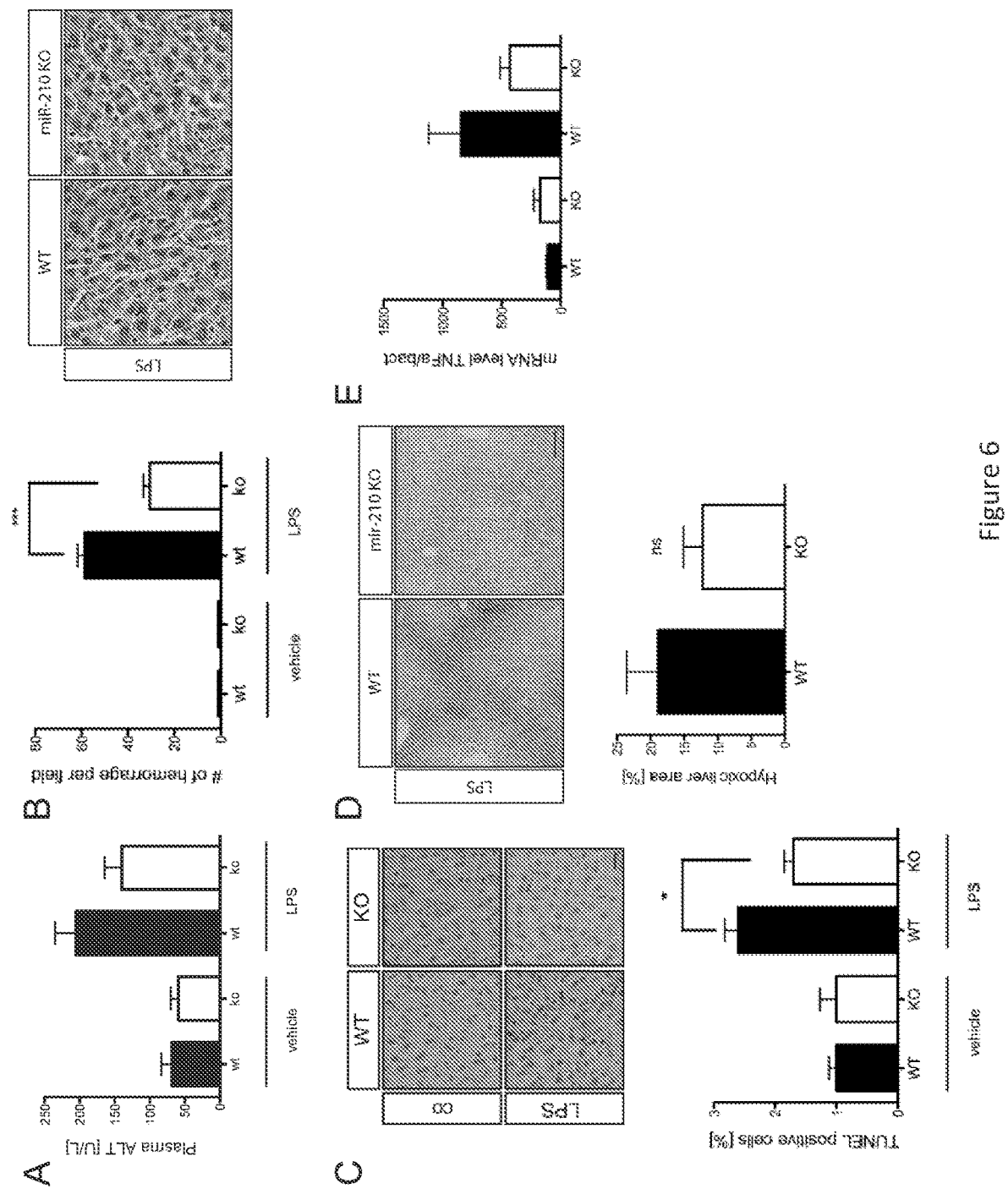
FIG. 6. miR-210 loss in macrophages is protective against LPS-induced liver damage. A. Quantification of plasma ALT values from blood samples taken 18 hours after injecting LPS (20 mg/kg) or PBS in miR-210 bone marrow transplanted WT or KO mice. B. Histological pictures of H&E staining from liver sections (right) of miR-210 WT or KO mice 18 hours after LPS (20 mg/kg) or PBS injection and quantification of the number of hemorrhages per field (left) based on the H&E staining (black arrow in histological picture). Scale bar, 20 μm. C. Results of TUNELapoptag staining (TUNEL positive cell is indicated with a black arrow) (upper panel) and analysis of the percentage of TUNEL positive cells in the liver (lower panel) of miR-210 WT or KO mice treated with LPS (20 mg/kg) or PBS for 18 hours. Scale bar, 100 μm. D. Histological pictures of PIMO immunostaining (upper panel) performed on liver samples of miR-210 KO and WT mice after an 18 hours treatment with LPS (20 mg/kg) or PBS and a histomorphometric quantification of the percentage of hypoxic area in the liver (lower panel) was performed. Scale bar, 100 μm. E. Quantification of the mRNA level by qPCR of the pro-inflammatory cytokine Tnfα from macrophages sorted from the liver of miR-210 WT or KO mice after treatment with LPS (20 mg/kg) for 8 hours. *$P<0.05$ ***$P<0.0005$.

Liver damage was investigated in miR-210 WT and KO mice using the plasma alanine transaminase (ALT) level (FIG. 6A), level of liver hemorrhage (FIG. 6B), the percentage of TUNEL positive cells (FIG. 6C) and the percentage of hypoxic liver area (FIG. 6D). The ALT level, which is a marker for decreased liver function, in the blood plasma of miR-210 WT mice was higher than the level in miR-210 KO mice (FIG. 6 A). We observed that the number of hemorrhages per field in the liver of miR-210 WT mice treated with LPS was significantly higher than the number in LPS treated miR-210 KO mice (FIG. 6B). Apoptosis assessed by the percentage of TUNEL positive cells was also higher under LPS treatment in miR-210 WT mice compared to the percentage in miR-210 KO mice. We checked the hypoxic area in the liver because it is known that inflammation is linked with tissue hypoxia. We observed that there was a trend towards a higher percentage of hypoxic area in the liver of LPS treated miR-210 WT mice (FIGS. 6 C and D). We checked the mRNA expression of the proinflammatory cytokine Tnfα in sorted macrophages from the liver of miR-210 WT and KO LPS treated or untreated mice to investigate if this factor might play a role in these differences in liver damage. Tnfα expression was higher under treatment in the WT mice compared to the KO mice, which indicates that the difference in liver damage might among others stem from the differences in Tnfa expression by macrophages present in the liver (FIG. 6E).

To conclude, the absence of miR-210 expression in the bone marrow may protect against organ damage, more specifically against liver and kidney damage, in mice with LPS-induced peritonitis.

Figure 7:
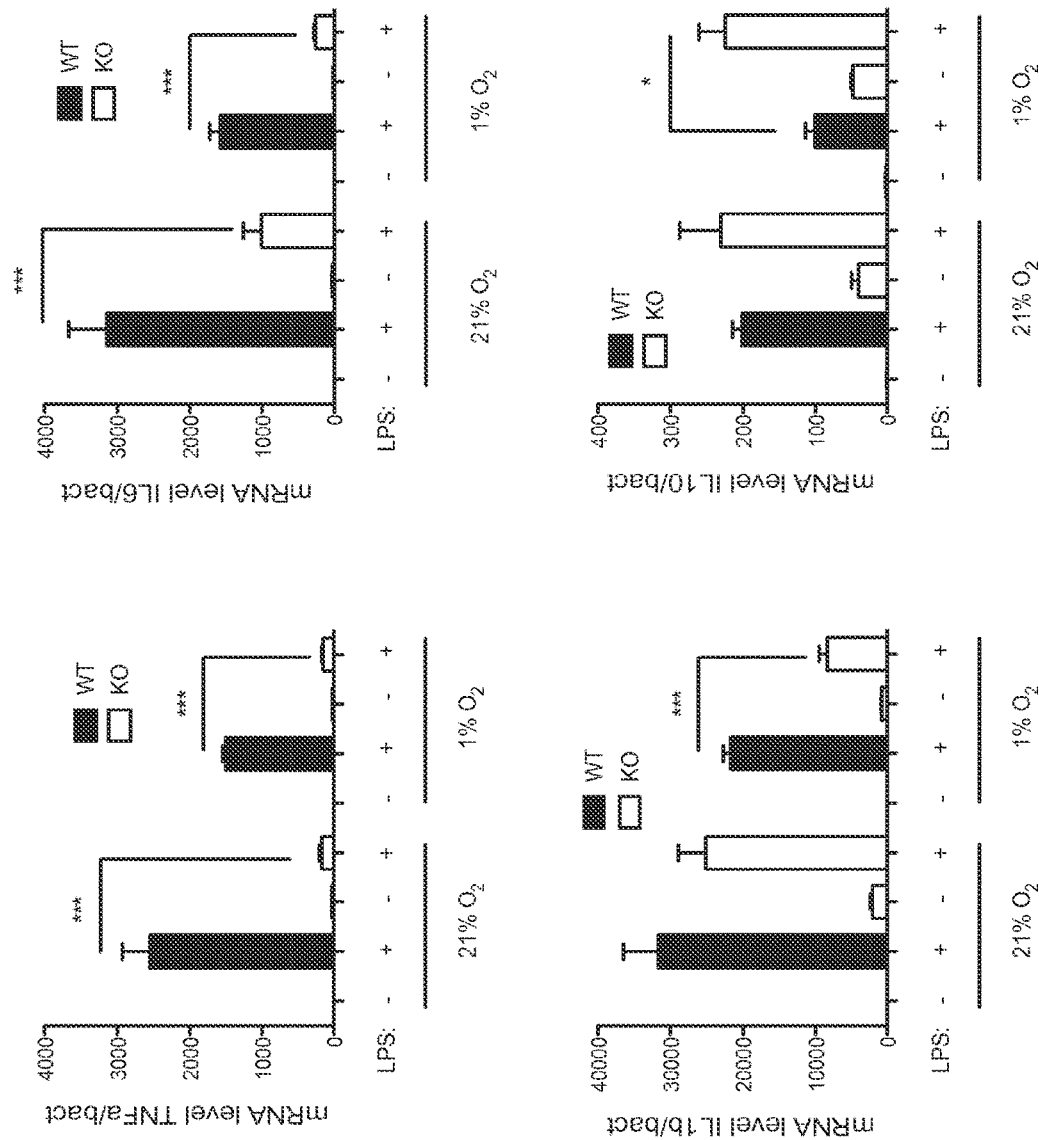
FIG. 7. Loss of miR-210 reduces the release of pro-inflammatory cytokines after LPS treatment and enhances anti-inflammatory cytokine release in PEMs. mRNA expression levels of the pro-inflammatory cytokines Tnfα (TNFα), Il-6 and Il-16 (IL-1b) and the anti-inflammatory cytokine Il-10 of miR-210 WT or KO PEMs treated +/−LPS (100 ng) for 4 hours and incubated in normoxia or hypoxia were analyzed by qPCR. βact expression was used to normalize the mRNA levels. *$P<0.05$ $P<0.005$ *$P<0.0005$.

Example 5. Loss of miR-210 in Macrophages Decreases the Release of LPS-Induced Pro-Inflammatory Cytokine To confirm the differences in inflammatory response between the two genotypes that we observed in vivo, we wanted to check the response of ex vivo peritoneal macrophages of miR-210 WT and miR-210 full KO mice to LPS. The mRNA levels of different pro-inflammatory (Tnfα, Il-6 and Il-1β) and an anti-inflammatory cytokine (Il-10) were measured using Q-RT PCR, after stimulating PEMs of miR-210 WT or miR-210 full KO mice for 4 hours with LPS (FIG. 7). The Tnfα and Il-6 levels were significantly higher in PEMs from miR-210 WT mice compared to PEMs from miR-210 KO mice (FIG. 7). This difference was observed both in normoxic and hypoxic conditions. The level of the pro-inflammatory cytokine Il-1β was only significantly higher in miR-210 WT PEMs when they were incubated in hypoxic conditions (FIG. 7). We also checked the mRNA level of the anti-inflammatory cytokine IL-10 and could show that the level of Il-10 in PEMs incubated at 1% oxygen was significantly lower in miR-210 WT macrophages (FIG. 7). However this difference was not seen in PEMs incubated in normoxic conditions. These results confirmed the differences between the miR-210 WT and KO mice in response to LPS, which we observed in the in vivo experiments. The loss of miR-210 reduces the release of the proinflammatory cytokines Tnfα, Il-6 and Il-1β and enhances the release of the anti-inflammatory cytokine Il-10 in hypoxic conditions after treatment with LPS. Because of that, loss of miR-210 expression in PEMs may protect against LPS-induced peritonitis.

Example 6. Loss of miR-210 Expression Enhances LPS/Zymosan Induced Phagocytosis

Figure 8:
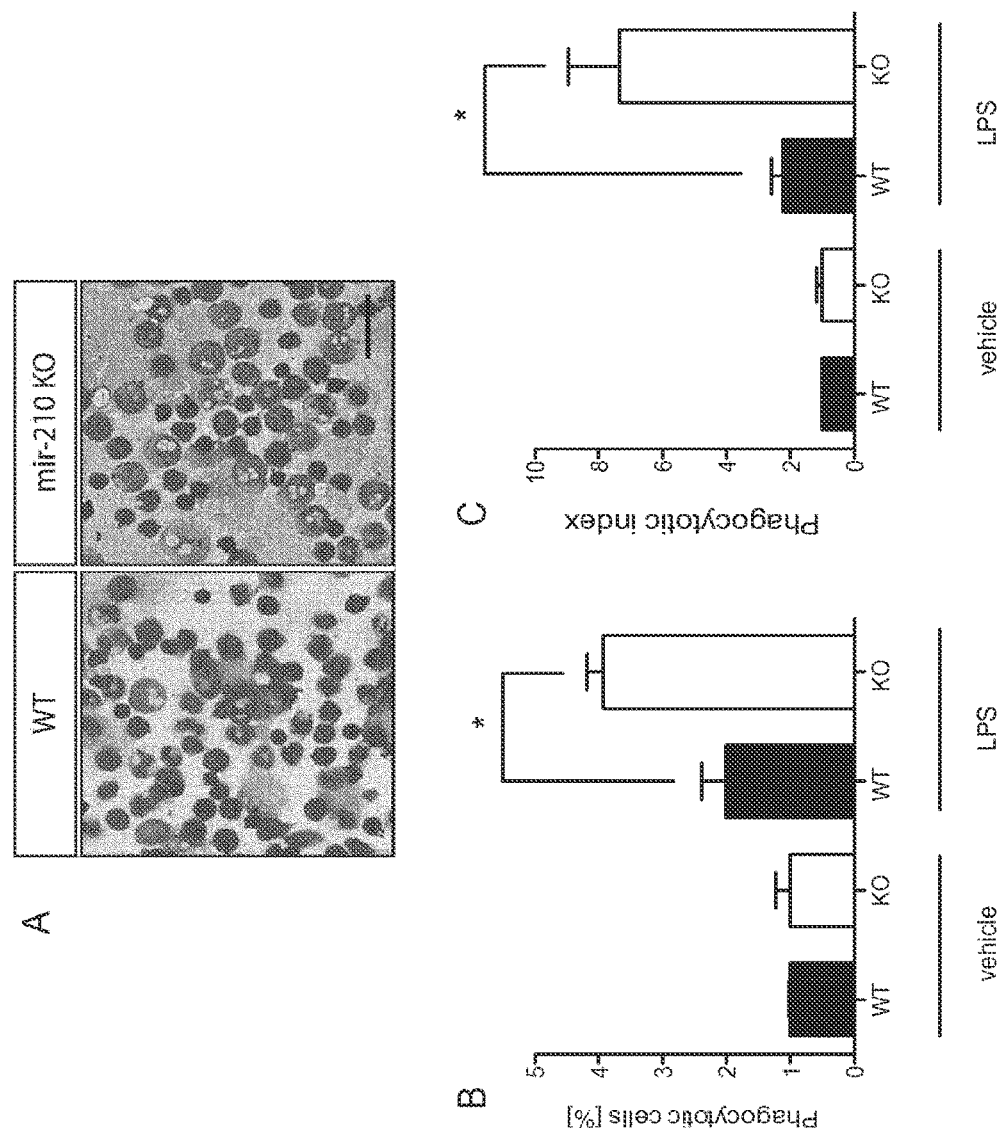
FIG. 8. More LPS/Zymosan induced phagocytosis is observed in miR-210 KO mice. A. Microscopic pictures of May-Grünwald-Giemsa stained PEMs derived from PBS or LPS (10 mg/kg) and zymosan (2 mg/kg) treated (for 4 hours) miR-210 WT or KO mice. Scale bar, 20 μm. (black arrows indicate the phagocytic particles) B. Percentage of phagocytic active miR-210 WT or KO PEMs treated with zymosan (2 mg/kg) and LPS (10 mg/kg) or PBS for 4 hours. C. Calculated phagocytic index (ratio of ingesting PEMs to non-ingesting PEMs multiplied by the average number of phagocytic particles per well) of PEMs in miR-210 WT or KO mice treated with LPS (10 mg/kg) and zymosan (2 mg/kg) or PBS for 4 hours. *$P<0.05$.

To investigate whether miR-210 deficiency changes the phagocytic activity of macrophages, which is an important function of macrophages, experimental peritonitis was induced in miR-210 WT or KO mice by injecting the mice intraperitoneally with LPS and yeast-derived b-glucan zymosan A. After 4 hours, PEMs were harvested and the percentage of phagocytic macrophages and phagocytic index via histomorphic analysis was determined (FIG. 8A). The percentage of phagocytic PEMs was significantly higher in miR-210 KO mice (FIG. 8B). The phagocytotic index was derived via multiplying the ratio of the counted ingesting macrophages and non-ingesting macrophages with the average number of phagocytosed particles per macrophage. After comparing the phagocytic index of PEMs derived from miR-210 WT and KO mice, we observed that the phagocytic index was significantly higher in PEMs derived from miR-210 KO mice (FIG. 8C). These results suggest that the phagocytic capacity is better in miR-210 KO mice, so the clearance of bacterial load may be better when there is loss of miR-210 expression in macrophages.

Figure 9:
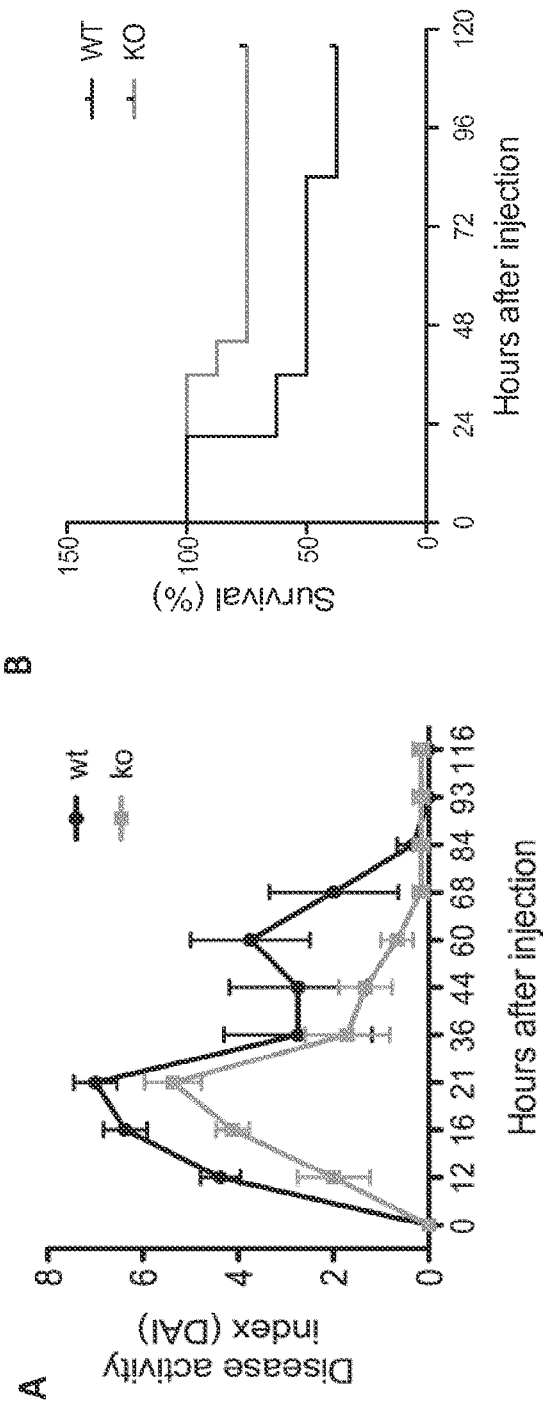
FIG. 9. Macrophage-specific loss of miR-210 improves the clinical symptoms and survival of LPS-induced peritonitis. (A) The severity of the clinical symptoms, represented by the disease activity index (DAI), was assessed at multiple time-points after injection of 15 mg/kg LPS. (B) Survival curve of WT and KO mice. Graphs show mean±SEM.

Example 7. Macrophage Specific Deletion of miR-210 Enhances the Survival in a Mouse Model of Sepsis To further study the role of miR-210 in an M1-like setting in vivo we used a sepsis model consisting of the induction of peritonitis by LPS injection. Previous results with chimeric mice (Example 3) informed us of the effect of the miR-210 deletion in the whole myeloid compartment. In order to confirm the macrophage origin of such effect we took advantage of the miR-210 LysZ.Cre mice. We continuously monitored the survival and the disease activity index (DAI), a readout of the clinical symptoms (hunched appearance, lethargy, shivering, closing of the eyes and tendency to lie down), in order to evaluate whether the macrophage specific loss of miR-210 influenced the course of the LPS-induced peritonitis. The DAI reached the maximum after 24 hours in both WT and KO mice, yet the score was significantly lower in KO mice (FIG. 9A), reflecting the less severe symptoms observed in these mice. At this point, almost 50% of WT mice and none of the KO mice had died (FIG. 9B). Afterwards, we observed full recovery of some mice and at the end of the experiment the survival percentage of WT and KO mice was 37.5% and 75%, respectively (FIGS. 9A and 9B). The experiment was finished when the clinical symptoms of the survivors completely disappeared (approximately after 120 hours).

These findings clearly indicate that specific loss of miR-210 in macrophages protects against LPS-induced peritonitis by decreasing the disease symptoms and improving the overall survival. Hence, they confirm the observations from Example 3 obtained in mice lacking miR-210 in the entire myeloid compartment.

Example 8. Anti-miR-210 Therapy Increases Survival of LPS-Treated Mice

Figure 10:
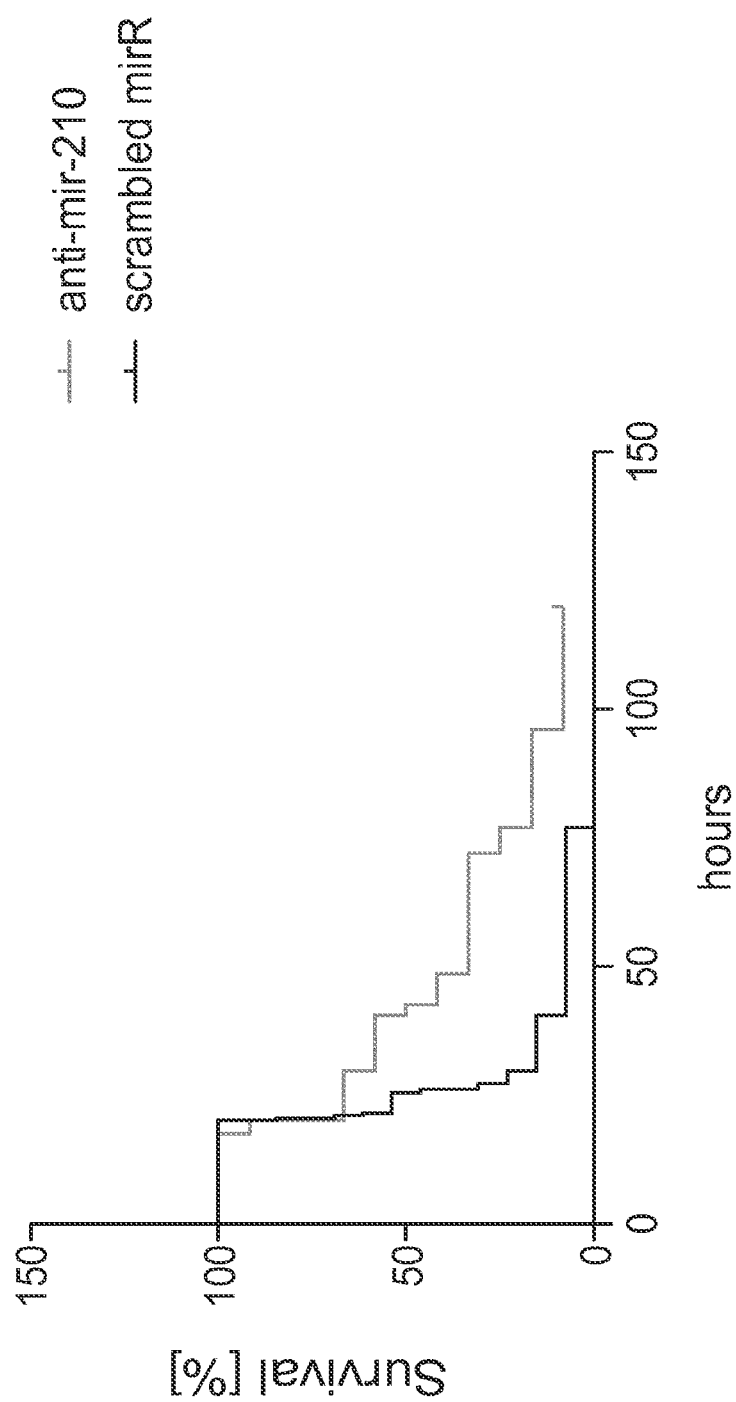
FIG. 10. Injection of miR-210 inhibitor improves survival of LPS-injected mice. Survival curve of anti-miR-210 treated mice (grey) and mice injected with scrambled oligonucleotides (black). miR-210 inhibitor and control (scrambled) treatment were performed 24 h prior to LPS injection.

To test whether the positive effect of genetically knocking-out miR-210 expression on survival of mice with LPS-induced peritonitis can be mimicked by anti-miR-210 therapy, an in vivo down modulation of miR-210 was carried out as previously described (Zaccagnini et al. 2014, Antioxidants and Redox Signaling 21:1177-1188). Briefly, 200 µl PBS-diluted locked nucleic acid (LNA) oligonucleotides (12 mg/kg) against miR-210 (anti-miR-210) or scrambled control sequences (SCR) were injected into the tail vein. 15 mers LNA-enhanced sequences with complete phosphothioate backbone were used (anti-miR-210: GCTGTCACACGCACA; SCR: CGTCTAGCCACCTAG) (In vivo LNA-microRNA Inhibitors; Exiqon). Given the very fast response upon LPS injection, it is unfeasible to therapeutically intervene with LPS-induced peritonitis. Therefore, the injection of LNA oligonucleotides was performed 48 hours prior to LPS injections. In line with our genetic experiments, anti-miR-210 treatment improved survival of LPS-treated mice (FIG. 10).

Example 9. miR-210 at the Crossroad of M1 and M2 Macrophage Polarization

In order to test the effect of loss of miR-210 expression in another M1 disease model, the response to *Trypanosoma brucei* infection was analysed in miR210 WT and KO mice. *Trypanosoma brucei* causes sleeping sickness in humans and Nagana in cattle. Mice were infected with *Trypanosoma brucei*. Tsetse flies infected with *T. brucei* AnTAR1 parasites were maintained at the Institute of Tropical Medicine. Mir-210$^{+/+}$ and mir-210$^{-/-}$ chimeric mice were infected with AnTat1.1E trypanosomes (intraperitoneally (i.p.)). Parasite and red blood cell (RBC) numbers in blood were determined via haemocytometer by tail-cut (2.5 ml blood in 500 ml RPMI). Anemia was expressed as percentage of RBCs remaining in infected mice compared to that of non-infected mice.

Figure 11:
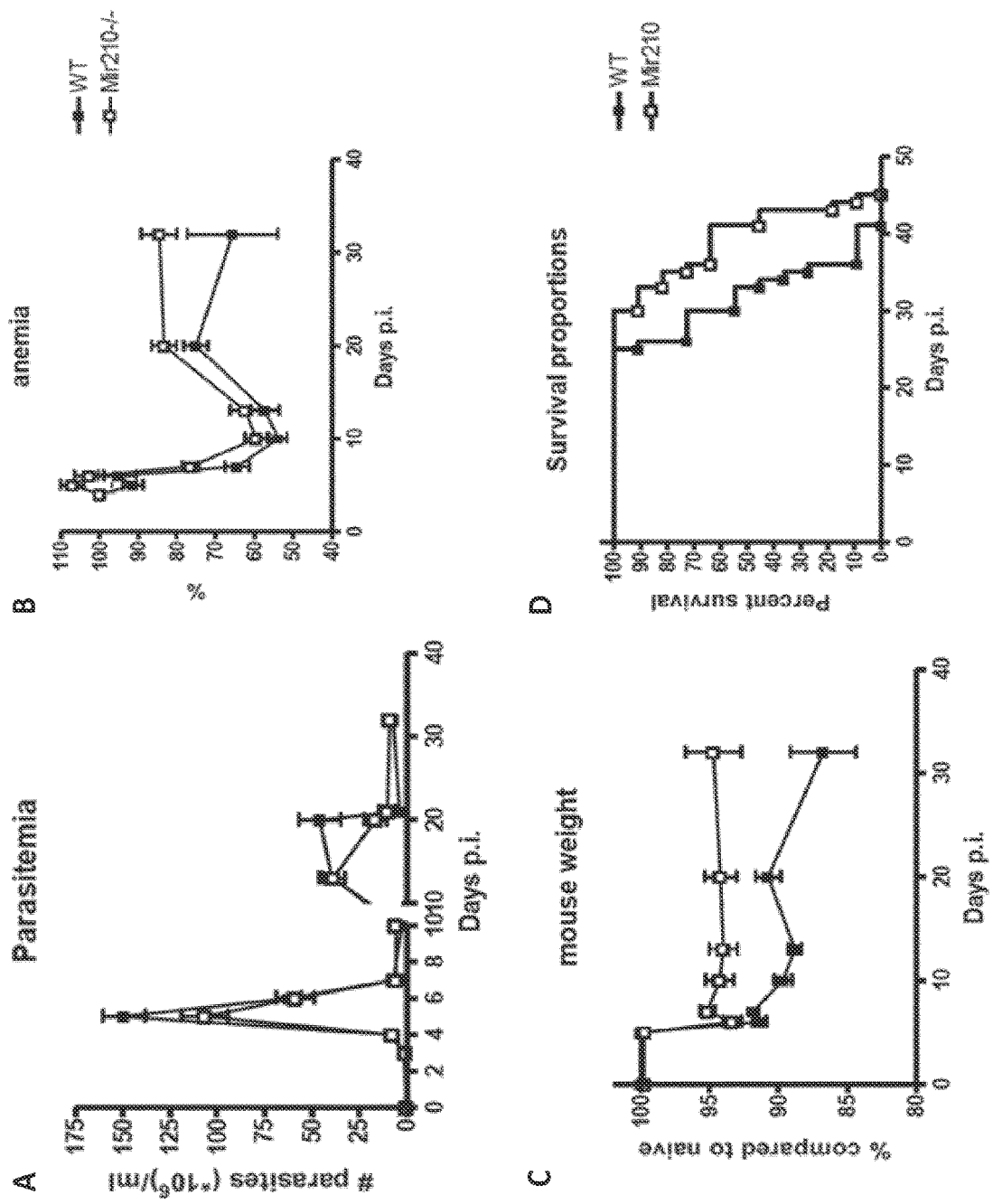
FIG. 11. Loss of miR-210 expression stimulates survival of *Trypanosoma brucei* infected mice. A) Parasitemia levels of infected miR-210 WT and KO mice. B-D) % anemia (B), mouse weight (C) and survival (D) of miR-210 WT and KO mice upon *T. brucei* infection.

First, the parasitemia level was analysed. Parasitemia is the quantitative content of parasites in the blood. It is generally used as a measurement of parasite load in the organism and is an indication of the degree of an active parasitic infection. During the progression of infection, parasitemia levels were similar between both mice groups, although the first peak parasitemia level was slightly higher in WT mice compared to miR-210 KO mice (FIG. 11A). Second, the level of anemia, the mouse weight and survival rate of the mice were analyzed. Surprisingly and in contrast to the small differences in parasitemia levels, a clear difference could be observed between miR-210 WT and KO mice. miR-210 mice exhibited less anemia during the chronic stage of infection, exhibited less weight loss compared to WT mice and miR-210 KO mice survived longer than WT mice (FIG. 11B-D). While the median survival time of WT mice was 33 days, the media survival time of miR-210 KO mice was 41 days (p-value=0.0022; 11 mice used per group). These results clearly show that loss of miR-210 expression positively affects survival of *Trypanosoma brucei* infested mice.

Figure 12:
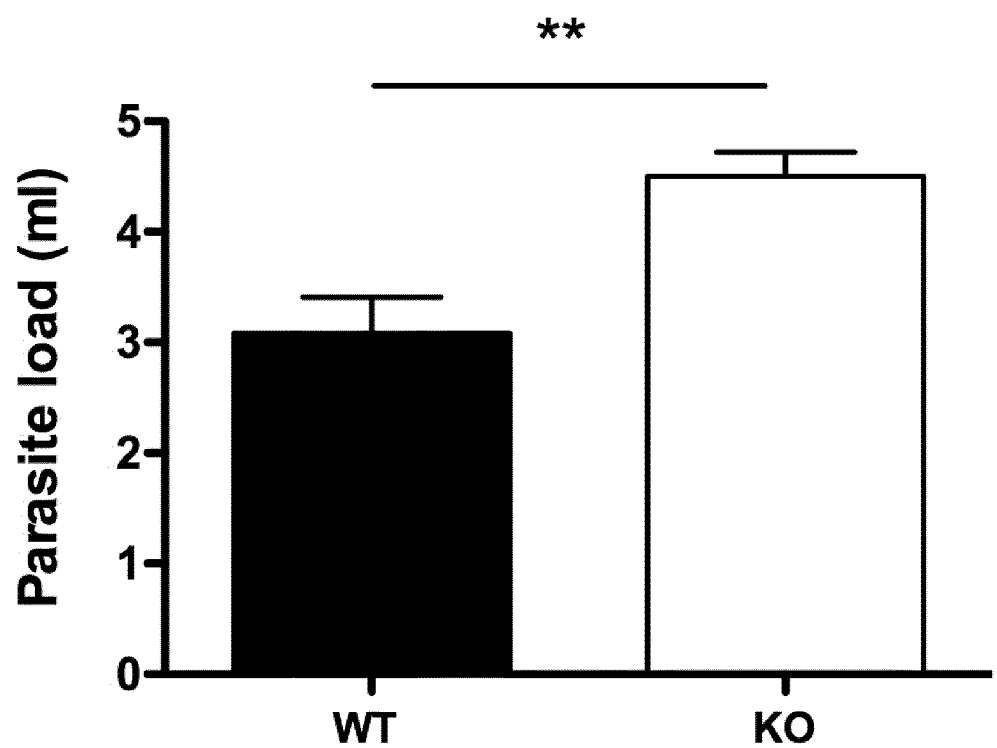
FIG. 12. Loss of miR-210 expression promotes M2 disease models. Parasite load following *T. crassiceps* infection in miR-210 WT and KO mice.

Given that LPS-induced systemic inflammation (sepsis) and *Trypanosoma brucei* infection are both examples of M1 disease models (inflammatory disease models characterized by macrophages with a M1-like phenotype), the effect of loss of miR-210 expression was also tested in a M2 disease model, more precisely *Taenia crassiceps* (tapeworm) infection. In contrast to *T. brucei* infection, loss of miR-210 expression positively affected disease progress. 12 weeks following *Taenia crassiceps* infections the parasite load was enhanced in miR-210 KO mice compared to WT mice (FIG. 12). These findings are in line with the observations that M2 cytokines suppress miR-210 expression (FIG. 2)

Materials and Methods

BM transplantation and hematological analysis: C56BL/6 recipient mice were sublethally irradiated with 9.5 Gy and subsequently received 1×10$^7$ bone marrow cells from mir-210$^{-/-}$ or mir-210$^{+/+}$ mice via tail vein injections in order to generate mir-210$^{-/-}$ or mir-210$^{+/+}$ chimeric mice. Reconstitution of the bone marrow was allowed for 6 weeks.

Bone marrow derived macrophages (BMDMs): Macrophages were derived from BM precursors as described before (Meerpohl et al., 1976). Briefly, BMDMs (2×10$^6$ cells/ml) were cultured in a volume of 5 ml in a 10 cm Petri dish (non tissue culture treated, bacterial grade) in DMEM supplemented with 20% FBS and 30% L929 conditioned medium as a source of M-CSF and 25 mM HEPES. After 3 days of culture, an additional 3 ml of differentiation medium was added. At day 7, macrophages were detached with ice cold PBS and characterized by FACS, using the pan-macrophage marker F4/80.

Histology and immunostaining: Livers and kidneys from septic mice were dissected, paraffin embedded, and sectioned at 8-µm thickness. For histological assessment of organ damage, sections were stained with H&E. Tumor hypoxia was detected 1 hr after i.p. injection of 60 mg/kg pimonidazole hydrochloride into tumor-bearing mice. Mice were sacrificed and tumors harvested. To detect the formation of pimonidazole adducts, tumor cryosections were immunostained with Hypoxyprobe-1-Mab1 (Hypoxyprobe kit, Chemicon) following the manufacturer's instructions. Periodic Acid Schiff (PAS) staining was performed to determine the glycogen positive area in the liver. After deparaffinization liver samples were incubated for 10 minutes in periodic acid (2 g H$_5$IO$_6$ in 200 ml AD), followed by a 3 min rins in tab water and 20 min incubation in Shiff's reagent (Prosan). The sections were counterstained with Harris's haematoxylin (BDH). For TUNEL stainings liver sections were stained using the ApoTag® Plus Peroxidase In Situ Apoptosis Detection Kit (Chemicon) according to the manufacturer's directions. Hematoxylin was used as a nuclear stain. Apoptosis was quantified as TUNEL positive cells per optical field. 5 20× fields per liver were selected in a blinded fashion for quantification.

Isolation of peritoneal macrophages: Mice were anesthetized with 30 µl intramuscular injections of nembutal. 6 ml PBS was injected into the peritoneal cavity using a 26 G needle. The abdomen was softly rubbed for 1-2 min and disinfected with 70% ethanol. Peritoneal exudate cells were collected by inserting a syringe via a 24 G needle. Retrieved cells were counted and seeded for the respected experiments. After one hour cells were washed once with PBS in order to enrich for macrophages.

LPS induced endotoxemia: 8 to 12 week old mice were injected with a single shot of 15-25 mg/kg LPS *Escherichia coli* 0111:B4 (Sigma Aldrich L2630). Mice were continuously monitored for survival. Clinical symptoms were scored according to their disease activity as previously described (Schaik and Abbas, Eur. J. Immunol, 2007). Blood was collected by retro-orbital bleeding 18 hours following LPS injections to determine plasma creatinine and ALT levels. In vivo down modulation of miR-210 was carried out as previously described (Zaccagnini et al., Antioxidants and Redox Signaling 2014). Briefly, 200 µl PBS-diluted LNA oligonucleotides (12 mg/kg) against miR-210 (anti-miR-210) or SCR control sequence were injected into the tail vein. 15mers LNA-enhanced sequences with complete phosphothioate backbone were used: anti-miR-210, GCTGTCACACGCACA (SEQ ID NO: 4); SCR, CGTCTAGCCACCTAG (SEQ ID NO: 5) (In vivo LNA-microRNA Inhibitors; Exiqon). The injection of LNA oligonucleotides was performed 48 hours prior LPS injections.

RNA extraction and reverse transcription: Cells were lysed and total RNA was isolated according to the manufacturer's instructions using the Cell and Plant Kit (Exiqon #300110). Gene specific reverse transcription of miR-210 and U6 snRNA was performed using TaqMan MicroRNA Reverse Transcription Kit (Applied Biosystems #4366597) and the gene specific RT primers from the microRNA assays (#000512 miR-210; #001973 U6 snRNA Applied Biosystems) according to the manufacturer's instructions. 200 to 500 ng of total RNA were converted to cDNA according to the manufacturer's instructions using QuantiTect Reverse Transcription kit (Qiagen, #205313). Protocol was adapted to the starting RNA quantity.

Disease models: Tsetse flies infected with *T. brucei* AnTAR1 parasites were maintained at the Institute of Tropical Medicine. Mir-210$^{+/+}$ and mir-210$^{-/-}$ chimeric mice were infected with AnTat1.1E trypanosomes (intraperitoneally (i.p.)). Parasite and red blood cell (RBC) numbers in blood were determined via haemocytometer by tail-cut (2.5 ml blood in 500 ml RPMI). Anemia was expressed as percentage of RBCs remaining in infected mice compared to that of non-infected mice.

To study cysticercosis, mice were inoculated intraperitoneally (ip) with 10 *Taenia crassiceps* cestodes, and peritoneal cells and helminths were collected at different time intervals post infection for further analysis.

The invention claimed is:

1. A method of treating sepsis or *Trypanosoma* infection in a subject, said method comprising:
   administering an inhibitor of miR-210 to said subject, wherein said inhibitor is an antisense oligomer, a siRNA, a shRNA, a gapmer, an antagomir, a morpholino, a locked nucleic acid, a peptide nucleic acid, or a ribozyme targeting the miR-210 micro RNA.

2. The method according to claim 1, wherein said inhibitor is part of a pharmaceutical composition comprising a pharmaceutically acceptable carrier.

3. A method of treating a subject presenting sepsis or *Trypanosoma* infection comprising determining the expression of miR-210 in macrophages of the subject;
   determining the expression of miR-210 in macrophages of a healthy control;
   detecting an increase of said expression of at least 10% in said subject compared to said healthy control;
   and administering an miR-210 inhibitor to the subject having an increase of miR-210 expression of at least 10%, wherein the inhibitor is an antisense oligomer, a siRNA, a shRNA, a gapmer, an antagomir, a morpholino, a locked nucleic acid, a peptide nucleic acid, a ribozyme, ZFN, a TALEN, a CRISPR-Cas, a CRISPR-C2c2, or a meganuclease targeting the miR-210 microRNA.

4. The method according to claim 3, comprising detecting an increase of said expression of at least 20% in said subject compared to said healthy control, and comprising administering the miR-210 inhibitor to a subject having an increase of miR-210 expression of at least 20%.

5. A method of treating sepsis or *Trypanosoma* infection in a subject, said method comprising:
   administering an inhibitor of miR-210 to said subject, wherein said inhibitor is a ZFN, a TALEN, a CRISPR-Cas, a CRISPR-C2c2 or a meganuclease targeting the miR-210 micro RNA.

\* \* \* \* \*

SEQUENCE LISTING

<160> NUMBER OF SEQ ID NOS: 5

<210> SEQ ID NO 1
<211> LENGTH: 110
<212> TYPE: RNA
<213> ORGANISM: Homo sapiens

<400> SEQUENCE: 1
acccggcagu gccuccaggc gcagggcagc cccugcccac cgcacacugc gcugccccag    60
acccacugug cgugugacag cggcugaucu gugccugggc agcgcgaccc             110

<210> SEQ ID NO 2
<211> LENGTH: 22
<212> TYPE: RNA
<213> ORGANISM: Homo sapiens

<400> SEQUENCE: 2
agccccugcc caccgcacac ug                                            22

<210> SEQ ID NO 3
<211> LENGTH: 22
<212> TYPE: RNA
<213> ORGANISM: Homo sapiens

<400> SEQUENCE: 3
cugugcgugu gacagcggcu ga                                            22

<210> SEQ ID NO 4
<211> LENGTH: 15
<212> TYPE: DNA
<213> ORGANISM: Artificial Sequence
<220> FEATURE:
<223> OTHER INFORMATION: anti-miR-210

<400> SEQUENCE: 4
gctgtcacac gcaca                                                    15

```
<210> SEQ ID NO 5
<211> LENGTH: 15
<212> TYPE: DNA
<213> ORGANISM: Artificial Sequence
<220> FEATURE:
<223> OTHER INFORMATION: scrambled RNA

<400> SEQUENCE: 5
cgtctagcca cctag                                                      15
```